(12) United States Patent
Ono et al.

(10) Patent No.: US 9,029,755 B2
(45) Date of Patent: May 12, 2015

(54) IMAGING SYSTEM WITH ILLUMINATION CONTROLLER TO VARIABLY CONTROL ILLUMINATION LIGHT

(71) Applicant: Olympus Medical Systems Corp., Tokyo (JP)

(72) Inventors: Wataru Ono, Tama (JP); Yusuke Yabe, Machida (JP); Tomoya Takahashi, Nishitokyo (JP); Kotaro Ogasawara, Nishitokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/223,224

(22) Filed: Mar. 24, 2014

(65) Prior Publication Data

US 2014/0203170 A1    Jul. 24, 2014

Related U.S. Application Data

(63) Continuation of application No. PCT/JP2013/061492, filed on Apr. 18, 2013.

(30) Foreign Application Priority Data

May 25, 2012  (JP) ................................. 2012-119814

(51) Int. Cl.
*H01L 27/00* (2006.01)
*G02B 26/02* (2006.01)
(Continued)

(52) U.S. Cl.
CPC ............ *G02B 26/02* (2013.01); *A61B 1/00006* (2013.01); *H01L 27/14601* (2013.01); *A61B 1/045* (2013.01); *A61B 1/0661* (2013.01)

(58) Field of Classification Search
CPC .......................... H01L 27/14601; G02B 26/02
USPC ................................................ 250/208.1, 205
See application file for complete search history.

(56) References Cited

U.S. PATENT DOCUMENTS 7,064,828 B1 *   6/2006   Rovira et al. ................. 356/369
2008/0027278 A1  1/2008   Mizuno
(Continued)

FOREIGN PATENT DOCUMENTS

JP     2007-318581     * 12/2007
JP     2008-029621 A    2/2008
(Continued)

OTHER PUBLICATIONS

International Search Report dated Jun. 18, 2013 issued in PCT/JP2013/061492.

(Continued)

*Primary Examiner* — Thanh Luu
(74) *Attorney, Agent, or Firm* — Scully, Scott, Murphy & Presser, P.C.

(57) ABSTRACT

An imaging system includes: an illumination unit configured to emit illumination light for illuminating a subject; a light receiving unit in which pixels are arranged two-dimensionally, each pixel being configured to receive light and generate an electric signal by performing photoelectric conversion of the light; a readout unit configured to sequentially read out the electric signal from the light receiving unit for every horizontal line; and an illumination controller configured to keep intensity of the illumination light emitted from the illumination unit constant in at least a part of a readout period where the readout unit reads out the horizontal line of the light receiving unit in one frame or one field period, and configured to variably control an illumination time of the illumination light emitted from the illumination unit, outside the readout period.

7 Claims, 17 Drawing Sheets

(51) Int. Cl.
  *A61B 1/00*     (2006.01)
  *H01L 27/146*   (2006.01)
  *A61B 1/045*    (2006.01)
  *A61B 1/06*     (2006.01)

(56) References Cited

U.S. PATENT DOCUMENTS

2009/0147077 A1   6/2009   Tani et al.
2012/0016200 A1   1/2012   Seto et al.
2012/0016201 A1   1/2012   Seto et al.

FOREIGN PATENT DOCUMENTS

JP   2009-136447 A   6/2009
JP   2011-206336 A   10/2011
JP   2012-019982 A   2/2012
JP   2012-019983 A   2/2012

OTHER PUBLICATIONS

Decision of a Patent Grant of JP 2013-546482 issued Dec. 12, 2013.

* cited by examiner

FIG.6
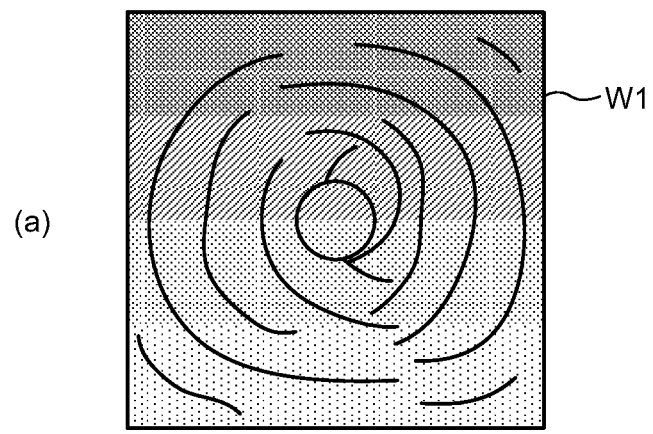
(a)
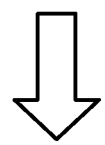
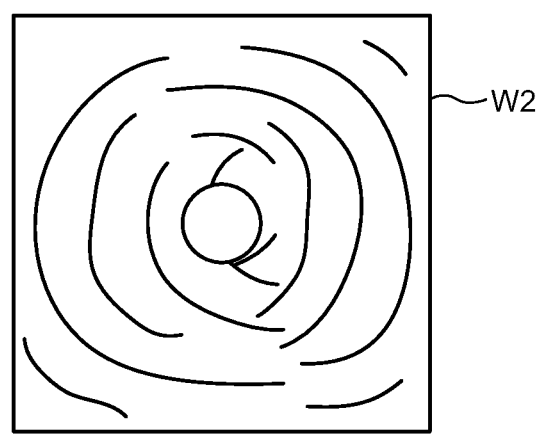
(b)

IMAGING SYSTEM WITH ILLUMINATION CONTROLLER TO VARIABLY CONTROL ILLUMINATION LIGHT

CROSS-REFERENCE TO RELATED APPLICATIONS

This application is a continuation of PCT international application Ser. No. PCT/JP2013/06192 filed on Apr. 18, 2013 which designates the United States, incorporated herein by reference, and which claims the benefit of priority from Japanese Patent Application No. 2012-119814, filed on May 25, 2012, incorporated herein by reference.

BACKGROUND OF THE INVENTION

1. Field of the Invention

The present invention relates to an imaging system that can output, as image information, an electric signal obtained by photoelectric conversion from a pixel specified arbitrarily as a readout target from among a plurality of pixels for image capture.

2. Description of the Related Art

Conventionally, an endoscope system has been used for observing organs of a subject, for example a patient, in the medical field. An endoscope system includes: a flexible, long and thin imaging device (electronic scope) to be inserted into a body cavity of a subject; an imaging element for capturing an in-vivo image, which is provided at an end of the imaging device; a light source device that emits illumination light that illuminates the subject; a processing device (external processor) that performs a specified image process on the in-vivo image captured by the imaging element; and a display device capable of displaying the in-vivo image on which the processing device has performed the image process. When the in-vivo image is obtained using the endoscope system, an insertion unit is inserted into the body cavity of the subject, the irradiation light is delivered to the biological tissue in the body cavity from the end of this insertion unit, and then the imaging element captures the in-vivo image. A user, for example a doctor, observes the organs of the subject through the in-vivo image displayed in the display device.

An example of the imaging element included in the endoscope system as above may be a CMOS (Complementary Metal Oxide Semiconductor) sensor. A CMOS sensor generates image data by a rolling shutter method in which exposure or readout is carried out while the timing is shifted for every line.

On the other hand, solid light sources such as an LED and a laser diode have been getting popular recently as the light source for illumination because of many advantages: the brightness of the light emitted can be easily changed by adjusting the current fed to the element; the size and power of the light source is smaller than those of a conventional lamp; and the response speed is high. It has been known that, however, the spectral characteristics of these light sources vary depending on the current value or the temperature; therefore, in order to avoid the variation, a method (PWM control) is employed in which the amount of illumination light is controlled not by the current but by the emission time. Thus, since the focusing mechanism for adjusting the amount of illumination light, which has been employed in the conventional halogen or xenon light source, is not necessary, the size reduction can be achieved and the omission of such an operation portion can reduce the occurrence of troubles.

Moreover, a technique is known that while there is a line in which charges of the imaging elements are read out, image capture is performed with the illumination light from a flash device turned off (see Japanese Laid-open Patent Publication No. 2008-29621).

SUMMARY OF THE INVENTION

In some embodiments, an imaging system includes: an illumination unit configured to emit illumination light for illuminating a subject; a light receiving unit in which pixels are arranged two-dimensionally, each pixel being configured to receive light and generate an electric signal by performing photoelectric conversion of the light; a readout unit configured to sequentially read out the electric signal from the light receiving unit for every horizontal line; and an illumination controller configured to keep intensity of the illumination light emitted from the illumination unit constant in at least a part of a readout period where the readout unit reads out the horizontal line of the light receiving unit in one frame or one field period, and configured to variably control an illumination time of the illumination light emitted from the illumination unit, outside the readout period.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 6 is a diagram representing the relation between the illumination light emitted from the light source device and the exposure period and the readout period of the imaging element during the image-capture time of the endoscope system according to the second modified example of the first embodiment of the present invention;

DETAILED DESCRIPTION OF THE PREFERRED EMBODIMENTS

Figure 1:
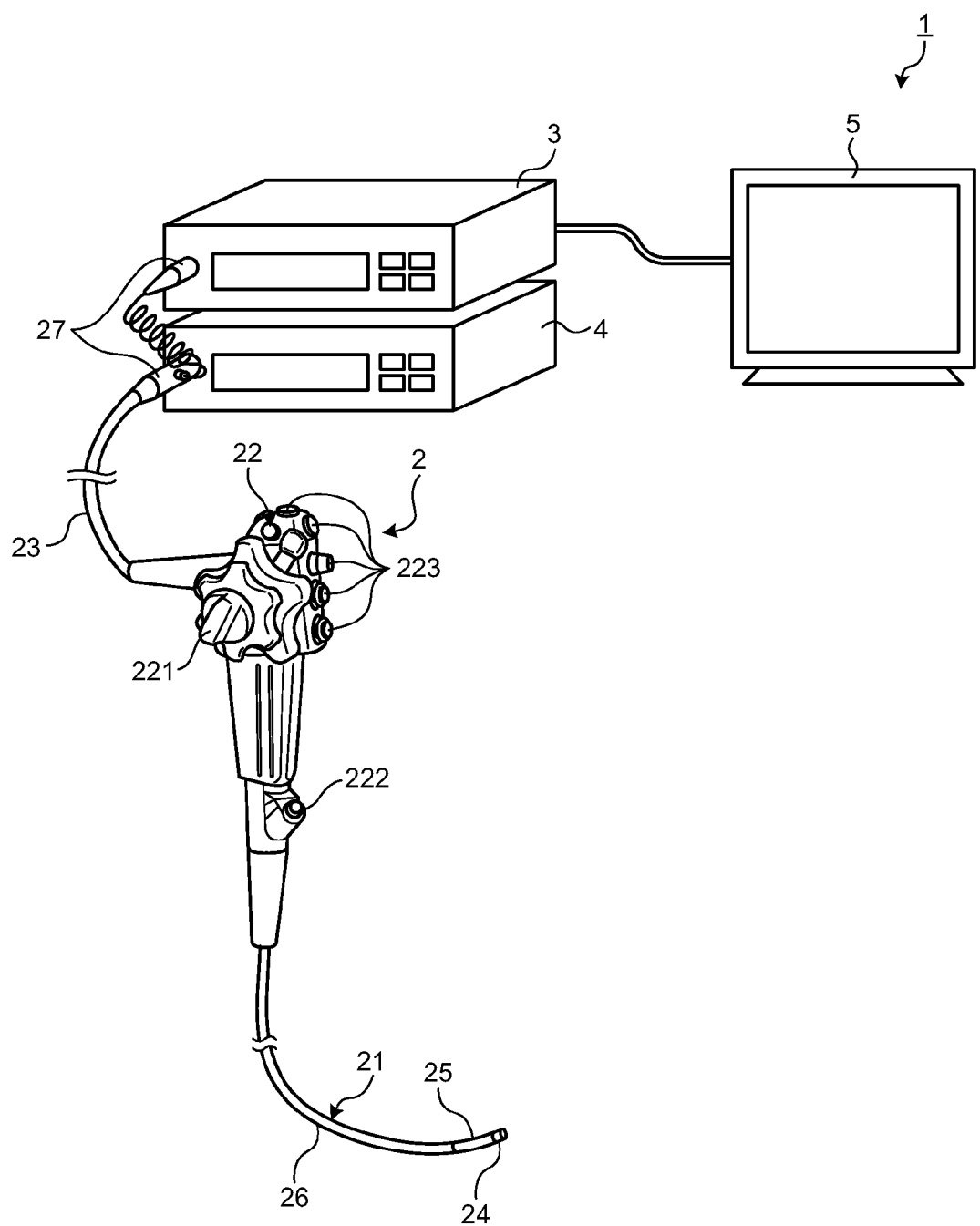
FIG. 1 is a diagram illustrating a schematic structure of an endoscope system according to a first embodiment of the present invention.

As modes for carrying out the invention (hereinafter referred to as "embodiments"), reference will be made below to an endoscope system for the medical use which captures and displays an image inside a body cavity of a subject such as a patient, as an imaging system. The present invention, however, is not limited to the embodiments. The same reference numerals are used to refer to the same parts throughout the drawings.

First Embodiment

Figure 2:
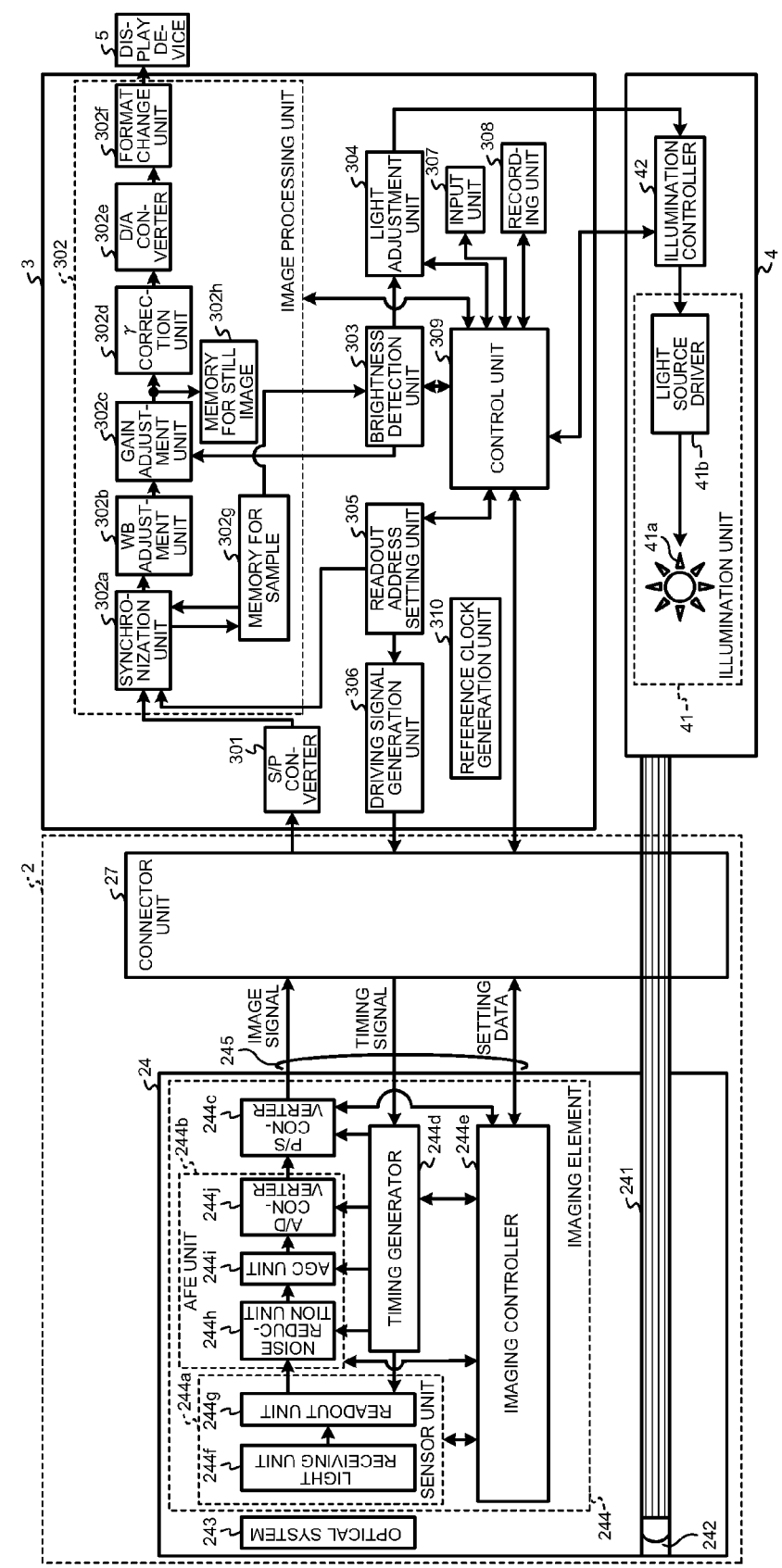
FIG. 2 is a block diagram illustrating a function structure of a main part of the endoscope system according to the first embodiment of the present invention.

FIG. 1 is a diagram illustrating a schematic structure of an endoscope system according to a first embodiment of the present invention. FIG. 2 is a block diagram illustrating a function structure of a main part of the endoscope system according to the first embodiment of the present invention.

As illustrated in FIG. 1 and FIG. 2, an endoscope system 1 includes: an endoscope 2 (electronic scope) whose end portion is to be inserted into a body cavity of a subject for capturing an in-vivo image of the subject; a processing device 3 (external processor) that performs a specified image process on the in-vivo image captured by the endoscope 2 and that generally controls the operation of the entire endoscope system 1; a light source device 4 that generates illumination light emitted from the end of the endoscope 2; and a display device 5 that displays the in-vivo image on which the processing device 3 has performed the image process.

The endoscope 2 includes: an insertion unit 21 that has a flexible, long, and thin shape; an operation unit 22 that is connected to a proximal end side of the insertion unit 21 and that accepts the input of various operation signals; and a universal cord 23 that extends from the operation unit 22 in a direction different from the direction where the insertion unit 21 extends, and that incorporates various cables connected to the processing device 3 and the light source device 4.

The insertion unit 21 includes: an end portion 24 that incorporates an imaging element 244 in which pixels that receive light and generate signals by performing photoelectric conversion on the received light are arranged two-dimensionally; a curved portion 25 that can be freely curved because of being formed of a plurality of curved pieces; and a flexible tube portion 26 that is connected to a proximal end side of the curved portion 25 and that has a flexible and longitudinal shape.

The end portion 24 includes: a light guide 241 that is formed using a glass fiber or the like and that guides light emitted from the light source device 4; an illumination lens 242 provided at an end of the light guide 241; a focusing optical system 243; and an imaging element 244 that is provided at the imaging position of the optical system 243 to receive light focused by the optical system 243 and that performs photoelectric conversion on the received light into an electric signal, thereby performing a specified signal process.

The optical system 243 is composed of one or more lenses, and has an optical zooming function that changes an angle of view and a focusing function that changes the focal point.

The imaging element 244 includes: a sensor unit 244a that outputs the electric signal obtained by photoelectric conversion of the light from the optical system 243; an analog front end unit 244b (hereinafter referred to as "AFE unit 244b") that removes noise from, or performs A/D conversion on the electric signal output from the sensor unit 244a; a P/S converter 244c that performs parallel/serial conversion on a digital signal (image signal) output from the AFE unit 244b and transmits the obtained signal to the outside; a timing generator 244d that generates a pulse for the driving timing of the sensor unit 244a or other various signal processes for the AFE unit 244b and the P/S converter 244c; and an imaging controller 244e that controls the operation of the imaging element 244. The imaging element 244 is a CMOS sensor.

The sensor unit 244a includes: a light receiving unit 244f in which pixels are arranged two-dimensionally, each pixel having a photodiode that accumulates charges according to the light quantity and an amplifier that amplifies the charges accumulated by the photodiode; and a readout unit 244g that reads out as the image information, the electric signal generated by the pixel set arbitrarily as the readout target among the plural pixels of the light receiving unit 244f. Moreover, a light reception plane of the light receiving unit 244f is provided with a color filter in each pixel.

The AFE unit 244b includes: a noise reduction unit 244h that reduces the noise component included in the electric signal (analog); an AGC (Auto Gain Control) unit 244i that adjusts the amplification factor (gain) of the electric signal to maintain a certain output level; and an A/D converter 244j that performs the A/D conversion on the electric signal as the image information (image signal) output via the AGC unit 244i. The noise reduction unit 244h reduces the noise using, for example, a correlated double sampling method.

The imaging controller 244e controls the operation of the end portion 24 in accordance with the setting data received from the processing device 3. The imaging controller 244e is composed of a CPU (central processing unit), a register that records various programs, or the like.

The operation unit 22 includes: a curving knob 221 that further curves the curved portion 25 horizontally and vertically; a tool insertion unit 222 through which a tool such as a forceps, a radio knife, or an inspection probe is inserted into a body cavity of a subject; and a plurality of switches 223 serving as an operation input unit to which an operation instruction signal for the processing device 3, the light source device 4, or other peripherals such as an air supplier, a water supplier, or a screen display controller is input. The tool inserted through the tool insertion unit 222 appears from an opening (not shown) through a tool channel (not shown) of the end portion 24.

The universal cord 23 includes at least the light guide 241 and a set of cables 245 including one or more signal lines. The universal cord 23 has a connector unit 27 that is attachable to or detachable from the processing device 3 and the light source device 4.

Next, a structure of the processing device 3 is described. The processing device 3 includes an S/P converter 301, an image processing unit 302, a brightness detection unit 303, a light adjustment unit 304, a readout address setting unit 305, a driving signal generation unit 306, an input unit 307, a recording unit 308, a control unit 309, and a reference clock generation unit 310.

The S/P converter 301 performs the serial/parallel conversion on the image signal (electric signal) input from the connector unit 27 and outputs the signal to the image processing unit 302.

Based on the image signal input from the S/P converter 301, the image processing unit 302 generates the in-vivo image to be displayed on the display device 5. The image processing unit 302 includes a synchronization unit 302a, a white balance adjustment unit 302b (hereinafter referred to as WB adjustment unit 302b), a gain adjustment unit 302c, a γ correction unit 302d, a D/A converter 302e, a format change unit 302f, a memory 302g for a sample, and a memory 302h for a still image.

The synchronization unit 302a synchronizes the image information input as the pixel information to be the RGB image information. The synchronization unit 302a sequentially outputs the synchronized RGB image information to the WB adjustment unit 302b and moreover outputs a part of the RGB image information to the memory 302g for a sample where the information is used to analyze the image, for example, to detect the brightness.

The WB adjustment unit 302b adjusts the white balance of the RGB image information. Specifically, the WB adjustment unit 302b adjusts the white balance of the RGB image information on the basis of the RGB image information.

The gain adjustment unit 302c adjusts the gain of the RGB image information. The gain adjustment unit 302c outputs the RGB signal on which the gain adjustment has been performed, to the γ correction unit 302d, and outputs a part of the RGB signal to the memory 302h for the still image where the signals are used for the still image display, the magnified image display, or the highlighted image display.

The γ correction unit 302d performs the gradation correction (γ correction) of the RGB image information for the display device 5.

The D/A converter 302e converts the RGB image information after the gradation correction, which has been output from the γ correction unit 302d, into the analog signal.

The format change unit 302f changes the image information, which has been converted into the analog signal in the D/A converter 302e, into the file format for the moving image of high definition, etc. and then outputs the information to the display device 5.

The brightness detection unit 303 detects the brightness level of each pixel on the basis of the RGB image information held by the memory 302g for a sample, and records the detected brightness level in the memory provided inside and moreover outputs the level to the control unit 309. The brightness detection unit 303 moreover calculates the gain adjustment value on the basis of the detected brightness level, and outputs the gain adjustment value to the gain adjustment unit 302c.

The light adjustment unit 304 sets the light quantity to be generated by the light source device 4, the light emission timing, or the like on the basis of the light irradiation amount calculated by the brightness detection unit 303 under the control of the control unit 309, and then outputs a light adjustment signal including this set condition to the light source device 4.

The readout address setting unit 305 has a function of setting the order of readout and the pixel as the readout target on the light reception plane of the sensor unit 244a. In other words, the readout address setting unit 305 has a function of setting the address of the pixel to be read out from the sensor unit 244a by the AFE unit 244b. The readout address setting unit 305 outputs the address information of the pixel set as the readout target, to the synchronization unit 302a.

The driving signal generation unit 306 generates a timing signal for driving the imaging element 244, and transmits the timing signal to the timing generator 244d via a specified signal line included in the set of cables 245. This timing signal includes the address information of the pixel as the readout target.

The input unit 307 accepts the input of various signals such as the operation instruction signal for instructing the operation of the endoscope system 1.

The recording unit 308 is realized using a semiconductor memory such as a flash memory or a DRAM (Dynamic Random Access Memory). The recording unit 308 records data including various programs for operating the endoscope system 1 and various parameters necessary for operating the endoscope system 1. Moreover, the recording unit 308 records the identification information of the processing device 3. Here, the identification information includes the unique information (ID), the year of manufacture, the specification information, the transmission method, and the transmission rate of the processing device 3, for example.

The control unit 309 is formed using a CPU or the like, and controls the driving of various components including the imaging element 244 and the light source device 4, and controls the input/output of the information relative to the components. The control unit 309 transmits the setting data for controlling the image capture to the imaging controller 244e via a specified signal line included in the set of cables 245. The control unit 309 outputs the synchronization signal including the exposure timing and the readout timing for each line of the imaging element 244 to the light source device 4.

The reference clock generation unit 310 generates a reference clock signal to be the reference of the operation of each component of the endoscope system 1, and supplies the generated reference clock signal to the component of the endoscope system 1.

Next, the structure of the light source device 4 is described. The light source device 4 includes an illumination unit 41 and an illumination controller 42.

The illumination unit 41 emits the illumination light for illuminating the subject. The illumination unit 41 includes a light source 41a and a light source driver 41b.

The light source 41a is formed of a white LED, and emits white light under the control of the illumination controller 42. The light generated from the light source 41a is delivered to the subject from the end portion 24 through a focusing lens (not shown) and the light guide 241.

The light source driver 41b causes the light source 41a to generate the white light by supplying current to the light source 41a under the control of the illumination controller 42.

The illumination controller 42 keeps the intensity of the illumination light emitted from the illumination unit 41 constant in at least a part of a readout period where the readout unit 244g reads out horizontal lines of the light receiving unit 244f in one frame or one field period; on the other hand, outside the readout period, the illumination controller 42 variably controls the intensity of the illumination light emitted from the illumination unit 41. Specifically, the illumination controller 42 performs PWM control on the intensity of the illumination light emitted from the illumination unit 41 in a period (exposure period) where the readout unit 244g does not read out the horizontal line of the light receiving unit 244f.

The display device 5 receives the in-vivo image generated by the processing device 3 through a video cable from the processing device 3 and displays the in-vivo image. The display device 5 is a liquid crystal display device or an organic EL (Electro Luminescence) display device.

Reference will be made to the relation between the illumination light from the light source device 4 and the timing of exposure or readout of the imaging element 244 during the image-capture time of the endoscope system 1 with the above structure.

Figure 3:
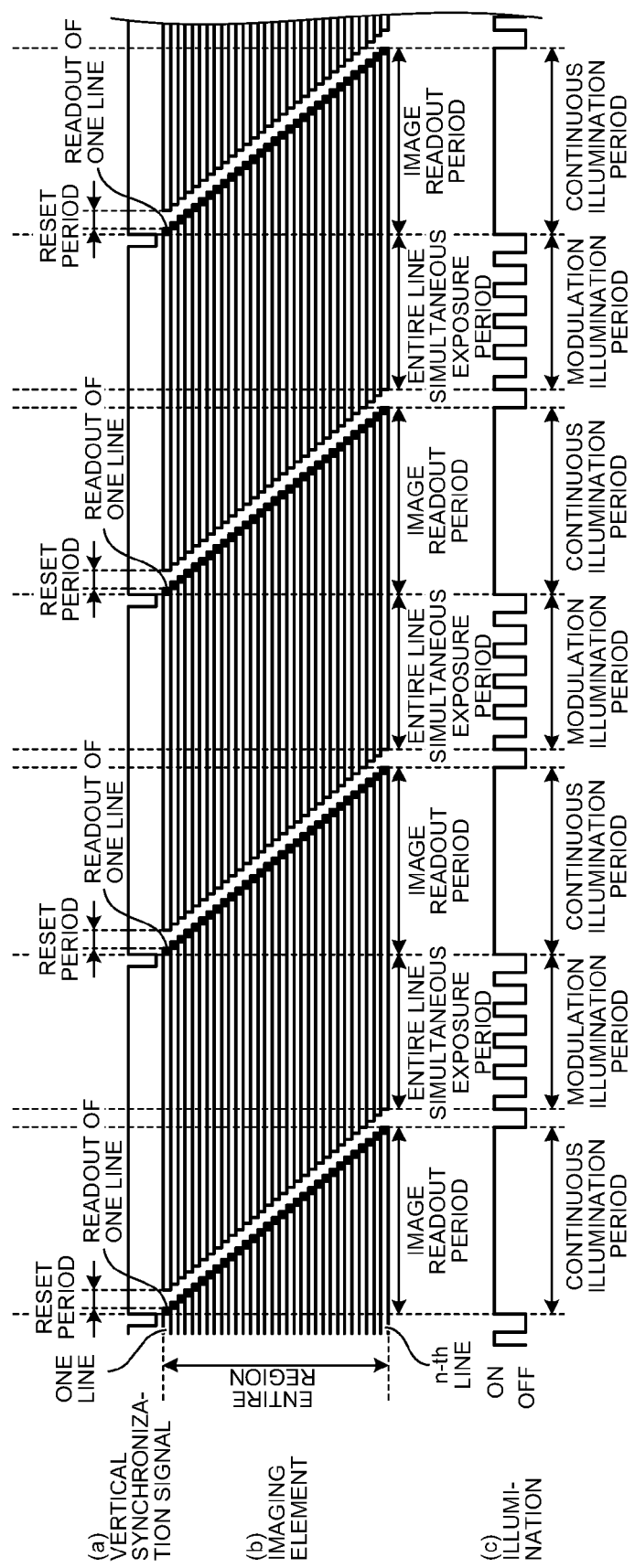
FIG. 3 is a diagram representing the relation between the illumination light emitted from the light source device and the exposure period and the readout period of the imaging element during the image-capture time of the endoscope system according to the first embodiment of the present invention.

FIG. 3 illustrates the relation between the illumination light emitted from the light source device 4 and the exposure period and the readout period of the imaging element 244 during the image-capture time of the endoscope system 1. In FIG. 3, (a) represents a vertical synchronization signal, (b) represents the exposure period and the readout timing of each line of the imaging element 244, and (c) represents the illumination period of the illumination light emitted from the light source device 4. Reference will be made below to the case in which all the lines including a dummy line in an optical black region or an invalid region of the imaging element 244 are sequentially read out from the top to the bottom in a progressive manner.

As illustrated in FIG. 3, when the plural frames are captured continuously, the imaging element 244 sequentially reads out the accumulated charges for every horizontal line. Specifically, the readout timing is different between the first line of the light receiving unit 244f that the readout unit 244g reads out first (first line in FIG. 3) and the n-th line of the light receiving unit 244f (n-th line in FIG. 3, n is a natural number) that the readout unit 244g reads out the last. Therefore, as illustrated in FIG. 3, the illumination controller 42 causes the illumination unit 41 to emit the continuous illumination light (CW illumination light) so that the intensity of the illumination light emitted from the illumination unit 41 is kept constant in the entire readout period (image readout period) where the readout unit 244g reads out the horizontal lines of the light receiving unit 244f in one frame period. This can certainly prevent the exposure unevenness for the horizontal lines of the light receiving unit 244f.

Meanwhile, as illustrated in FIG. 3, the illumination controller 42 modulates the intensity of the illumination light emitted from the illumination unit 41 in the entire line simultaneous exposure period, which is the period outside the period where the readout unit 244g reads out the horizontal lines of the light receiving unit 244f in one frame period. Specifically, the illumination controller 42 performs the PWM control on the illumination unit 41 so that the illumination light is emitted in the entire line simultaneous exposure period of the light receiving unit 244f. This can prevent the change in color temperature depending on the characteristic of the light source 41a.

In the first embodiment of the present invention described above, the illumination controller 42 keeps the intensity of the illumination light emitted from the illumination unit 41 constant in at least a part of the readout period where the readout unit 244g reads out the horizontal lines of the light receiving unit 244f in one frame period, and on the other hand, the illumination controller 42 variably controls the intensity of the illumination light emitted from the illumination unit 41 in the entire line simultaneous exposure period, which is the period outside the readout period. As a result, the exposure unevenness of the image can be certainly prevented.

Note that in the first embodiment, the illumination controller 42 may variably control the intensity of the illumination light emitted from the illumination unit 41 for every frame on the basis of the brightness of the subject input from the light adjustment unit 304.

First Modified Example of First Embodiment

Figure 4:
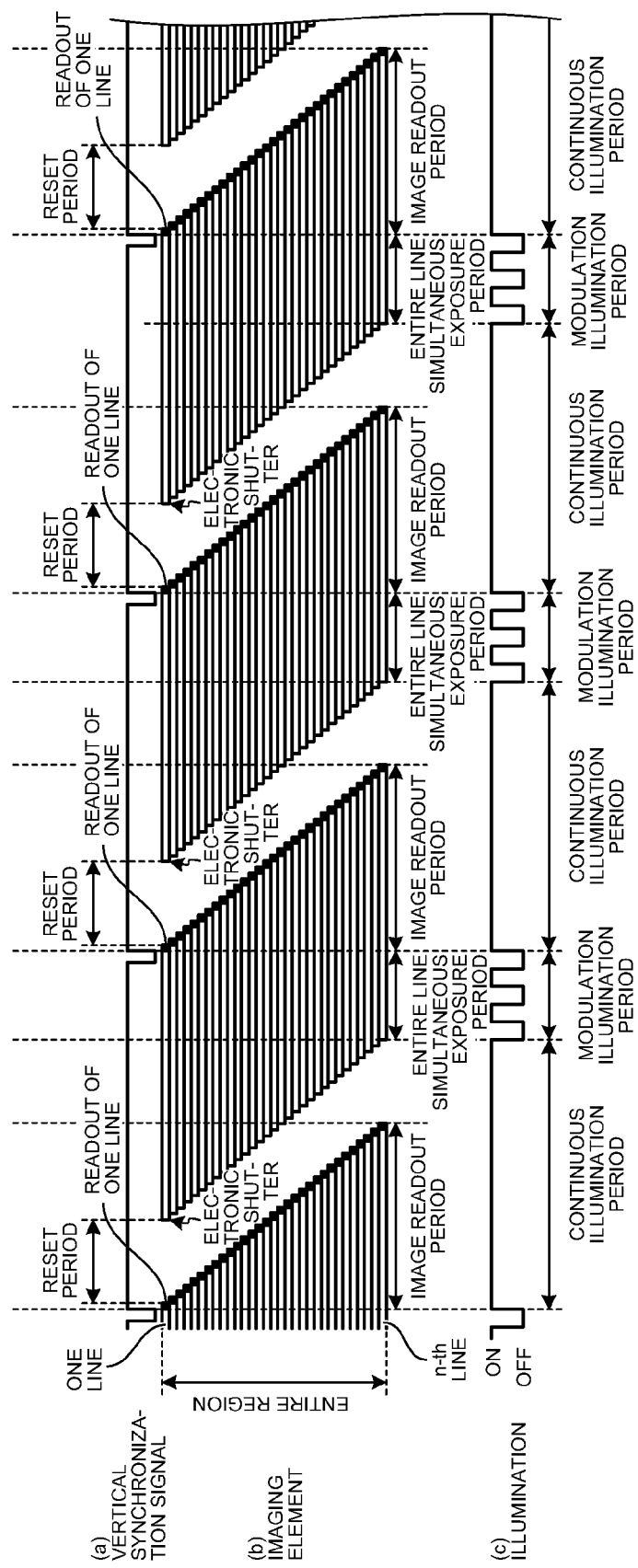
FIG. 4 is a diagram representing the relation between the illumination light emitted from the light source device and the exposure period and the readout period of the imaging element during the image-capture time of the endoscope system according to a first modified example of the first embodiment of the present invention.

FIG. 4 is a diagram illustrating a relation between the illumination light emitted from the light source device 4 and the exposure period and the readout period of the imaging element 244 during the image-capture time of the endoscope system 1 according to a first modified example of the first embodiment of the present invention. In FIG. 4, (a) represents a vertical synchronization signal, (b) represents the exposure period and the readout timing of each line of the imaging element 244, and (c) represents the illumination period of the illumination light emitted from the light source device 4.

As illustrated in FIG. 4, after the readout of each horizontal line of the light receiving unit 244f is started with an electronic shutter under the control of the imaging controller 244e, the readout unit 244g sequentially reads out the charges accumulated in the light receiving unit 244f for every horizontal line. Therefore, as illustrated in FIG. 4, the illumination controller 42 performs the PWM control on the illumination unit 41 so that the illumination unit 41 emits the illumination light in the entire line simultaneous exposure period that is after the electronic shutter of the last n-th line of the light receiving unit 244f ends and before the readout unit 244g reads out the first line of the light receiving unit 244f in one frame period.

Meanwhile, the illumination controller 42 causes the illumination unit 41 to continuously emit the illumination light so that the intensity of the illumination light emitted from the illumination unit 41 is kept constant in a period after the readout unit 244g starts to read out the first line of the light receiving unit 244f and before the electronic shutter of the last n-th line of the light receiving unit 244f ends in one frame period.

According to the first modified example of the first embodiment of the present invention described above, the illumination unit 41 can be operated by the PWM control even when the electronic shutter is used in combination; therefore, the exposure unevenness of the image can be prevented certainly while the color temperature of the light and the like that depend on the characteristics of the light source 41a are kept constant.

Second Modified Example of First Embodiment

Figure 5:
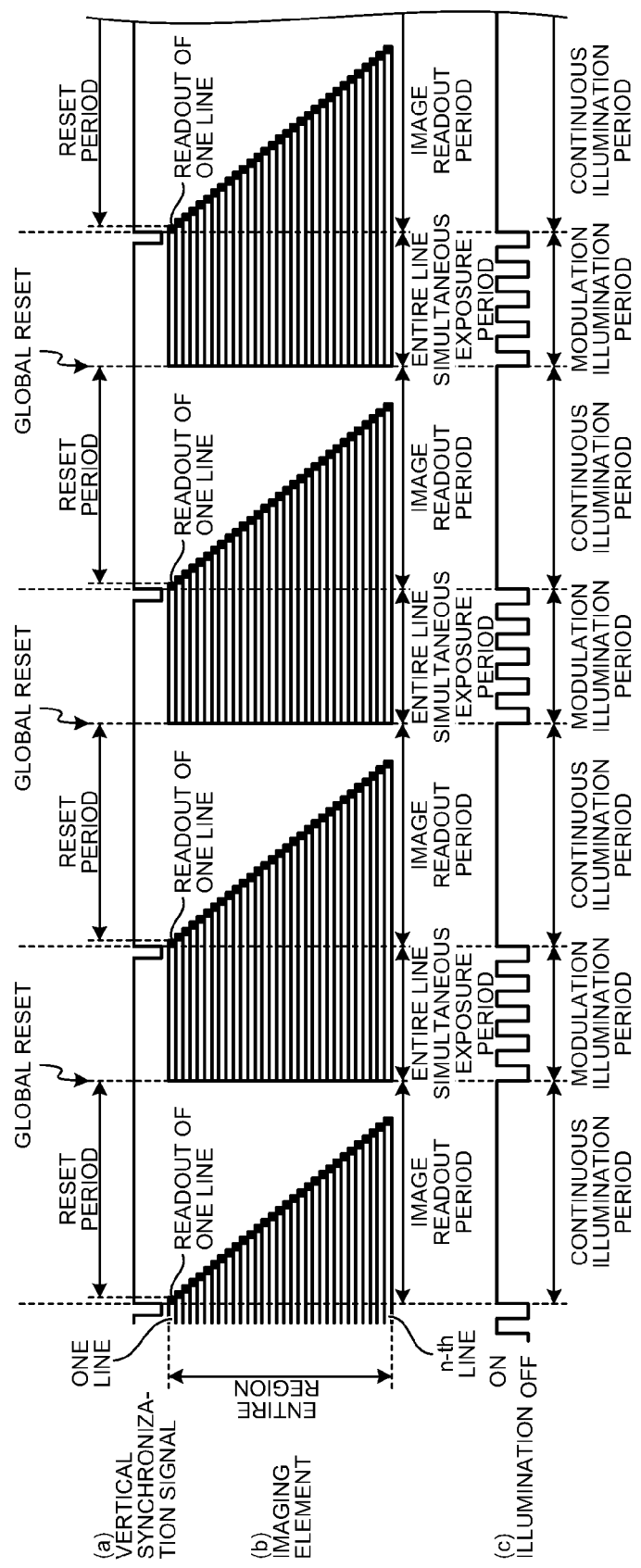
FIG. 5 is a diagram representing the relation between the illumination light emitted from the light source device and the exposure period and the readout period of the imaging element during the image-capture time of the endoscope system according to a second modified example of the first embodiment of the present invention.

FIG. 5 is a diagram illustrating the relation between the illumination light emitted from the light source device 4 and the exposure period and the readout period of the imaging element 244 during the image-capture time of the endoscope system 1 according to a second modified example of the first embodiment of the present invention. In FIG. 5, (a) represents a vertical synchronization signal, (b) represents the exposure period and the readout timing of each line of the imaging element 244, and (c) represents the illumination period of the illumination light emitted from the light source device 4.

As illustrated in FIG. 5, the light receiving unit 244f starts to expose after having conducted the global reset in a specified cycle under the control of the imaging controller 244e. Here, the global reset refers to the operation of resetting the charges accumulated in each line of the light receiving unit 244f at the same time. After that, the readout unit 244g sequentially reads out the charges accumulated in the light receiving unit 244f for every horizontal line. Therefore, as illustrated in FIG. 5, the illumination controller 42 performs the PWM control on the illumination unit 41 so that the illumination unit 41 emits the illumination light in the entire line simultaneous exposure period that is after the light receiving unit 244f conducts the global reset and before the readout unit 244g reads out the first line of the light receiving unit 244f in one frame period.

Meanwhile, the illumination controller 42 causes the illumination unit 41 to continuously emit the illumination light so that the intensity of the illumination light emitted from the illumination unit 41 is kept constant in a period after the readout unit 244g starts to read out the first line of the light receiving unit 244f and before the global shutter of the light receiving unit 244f starts in one frame period.

Therefore, at the stage in which the readout unit 244g has read out of each line of the light receiving unit 244f, the exposure unevenness occurs in the acquired image W1 as illustrated in FIG. 6(a). Specifically, the brightness is different in the first line and the last line of the acquired image W1. In view of this, the control unit 309 acquires the exposure time of each line of the imaging element 244 and has the image processing unit 302 correct the brightness according to the exposure time of each line of the imaging element 244 on the basis of the acquired exposure time. Specifically, as illustrated in FIG. 6(b), the image processing unit 302 generates a corrected image W2 by adjusting the width of the gain on the basis of the exposure time of each line of the imaging element 244 and then performing γ correction. Thus, the image with no exposure unevenness can be obtained.

According to the second modified example of the first embodiment of the present invention described above, the illumination unit 41 can be operated by the PWM control even when the global shutter is used in combination; therefore, the exposure unevenness of the image can be prevented certainly while the color temperature of the light and the like that depend on the characteristic of the light source 41a are kept constant.

Third Modified Example of First Embodiment

Figure 7:
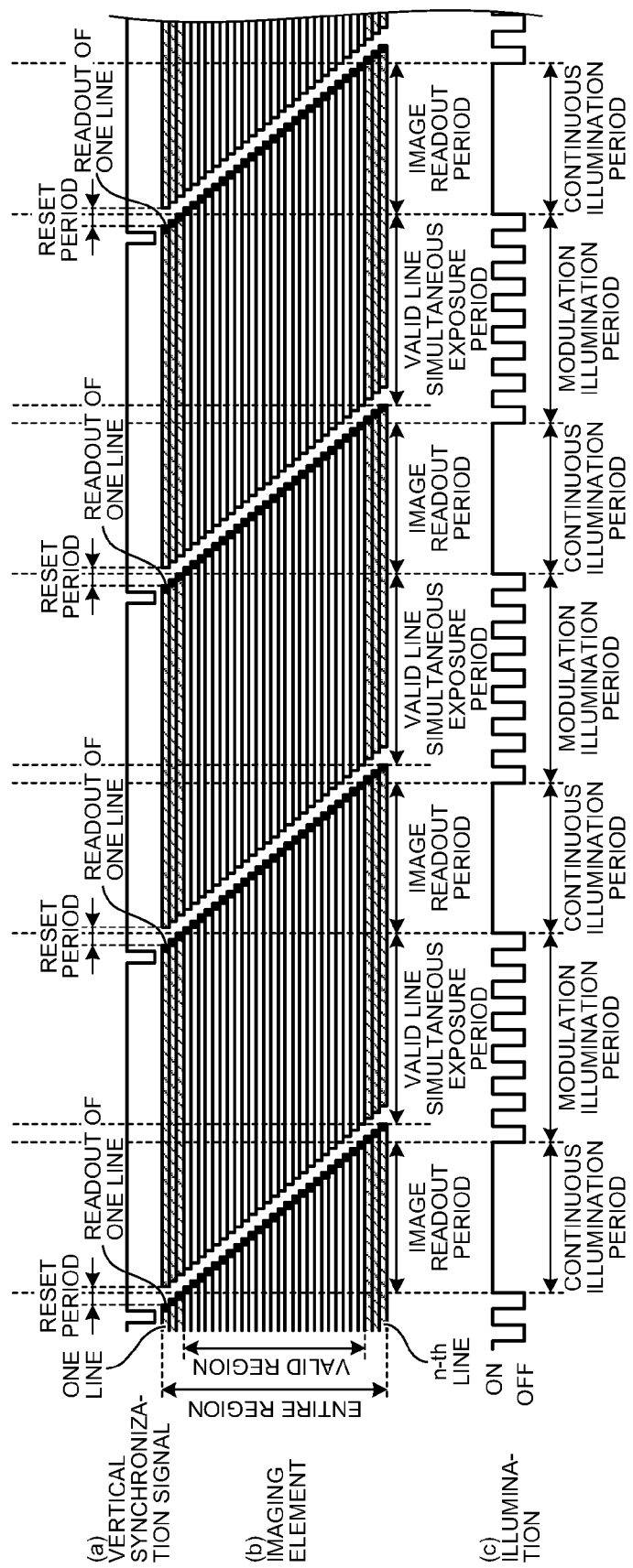
FIG. 7 is a diagram representing the relation between the illumination light emitted from the light source device and the exposure period and the readout period of the imaging element during the image-capture time of the endoscope system according to a third modified example of the first embodiment of the present invention.

FIG. 7 is a diagram illustrating the relation between the illumination light emitted from the light source device 4 and the exposure period and the readout period of the imaging element 244 during the image-capture time of the endoscope system 1 according to the third modified example of the first embodiment of the present invention. In FIG. 7, (a) represents a vertical synchronization signal, (b) represents the exposure period and the readout timing of each line of the imaging element 244, and (c) represents the illumination period of the illumination light emitted from the light source device 4.

As illustrated in FIG. 7, the illumination controller 42 causes the illumination unit 41 to continuously emit the illumination light so that the intensity of the illumination light emitted from the illumination unit 41 is kept constant in a period after the readout unit 244g starts to read out the first line in a valid region of the light receiving unit 244f and before the readout of the last line in the valid region ends in one frame period. Here, the valid region refers to a region of the light receiving unit 244f on which the image processing unit 302 performs the image process.

Meanwhile, the illumination controller 42 performs the PWM control on the illumination unit 41 so that the illumination unit 41 emits the illumination light in a valid line simultaneous exposure period that is after the readout unit 244g finishes readout of the last line in the valid region of the light receiving unit 244f and before the readout unit 244g starts to read out the first line in the valid region in one frame period.

According to the third modified example of the first embodiment of the present invention described above, continuous illumination is employed in which the illumination light of the illumination unit 41 is kept constant only in the lines in the valid region of the light receiving unit 244f; therefore, the exposure unevenness of the image can be prevented certainly while the color temperature of the light and the like that depend on the characteristic of the light source 41a are kept constant.

Moreover, according to the third modified example of the first embodiment of the present invention described above, since the illumination controller 42 can perform the PWM control on the illumination unit 41 only in the simultaneous exposure period of the lines in the valid region of the light receiving unit 244f, the modulation illumination period can be set long.

Fourth Modified Example of First Embodiment

Figure 8:
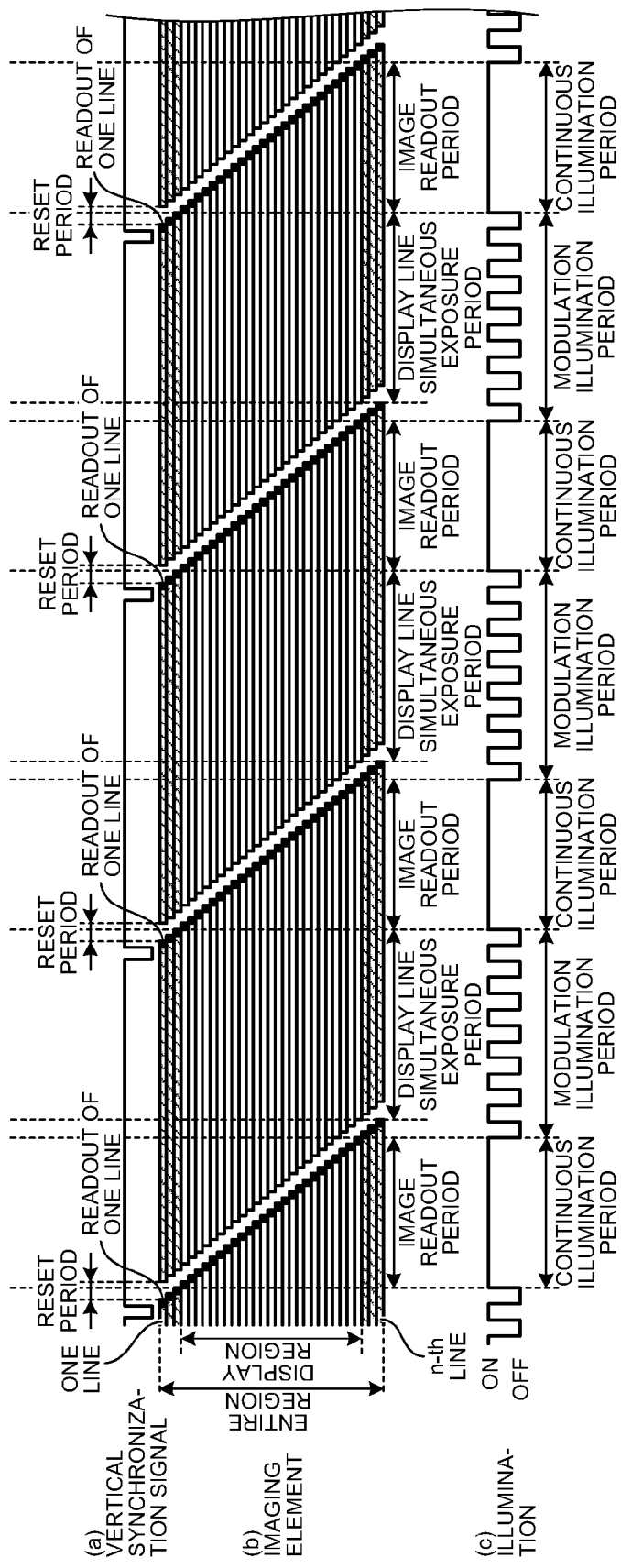
FIG. 8 is a diagram representing the relation between the illumination light emitted from the light source device and the exposure period and the readout period of the imaging element during the image-capture time of the endoscope system according to a fourth modified example of the first embodiment of the present invention.

FIG. 8 is a diagram illustrating the relation between the illumination light emitted from the light source device 4 and the exposure period and the readout period of the imaging element 244 during the image-capture time of the endoscope system 1 according to a fourth modified example of the first embodiment of the present invention. In FIG. 8, (a) represents a vertical synchronization signal, (b) represents the exposure period and the readout timing of each line of the imaging element 244, and (c) represents the illumination period of the illumination light emitted from the light source device 4.

As illustrated in FIG. 8, the illumination controller 42 causes the illumination unit 41 to continuously emit the illumination light so that the intensity of the illumination light emitted from the illumination unit 41 is kept constant in a period after the readout unit 244g starts to read out the first line in a display region of the light receiving unit 244f and before the readout of the last line in the display region ends in one frame period. Here, the display region corresponds to the region of the light receiving unit 244f on which the image processing unit 302 performs the image process and to the in-vivo image displayed in the display device 5.

Meanwhile, the illumination controller 42 performs the PWM control on the illumination unit 41 so that the illumination unit 41 emits the illumination light in a display line simultaneous exposure period after the readout unit 244g finishes readout of the last line in the display region of the light receiving unit 244f and before the readout unit 244g starts to read out the first line in the display region in one frame period.

According to the fourth modified example of the first embodiment of the present invention described above, continuous illumination is employed in which the illumination light of the illumination unit 41 is kept constant only in the lines in the display region of the light receiving unit 244f; therefore, the exposure unevenness of the image can be prevented certainly while the color temperature of the light and the like that depend on the characteristic of the light source 41a are kept constant.

Moreover, according to the fourth modified example of the first embodiment of the present invention described above, the illumination controller 42 performs the PWM control on the illumination unit 41 only in the display line simultaneous exposure period of the lines in the display region of the light receiving unit 244f so that the illumination unit 41 emits the illumination light. Therefore, the modulation illumination period in which the illumination unit 41 is subjected to the PWM control can be set longer than the valid line simultaneous exposure period in the valid region of the light receiving unit 244f.

Second Embodiment

Next, a second embodiment of the present invention is described. In the endoscope system according to the second embodiment, when the control is switched from the variable control for the illumination time of the light source device to the variable control for the intensity of the illumination light, that switching is conducted so that the intensity of the illumination light is changed continuously. Therefore, the endoscope system according to the second embodiment is described first and then, the illumination method for the light source device during the image-capture time of the endoscope system is described. The same reference numerals are used to refer to the same parts as those of the first embodiment.

Figure 9:
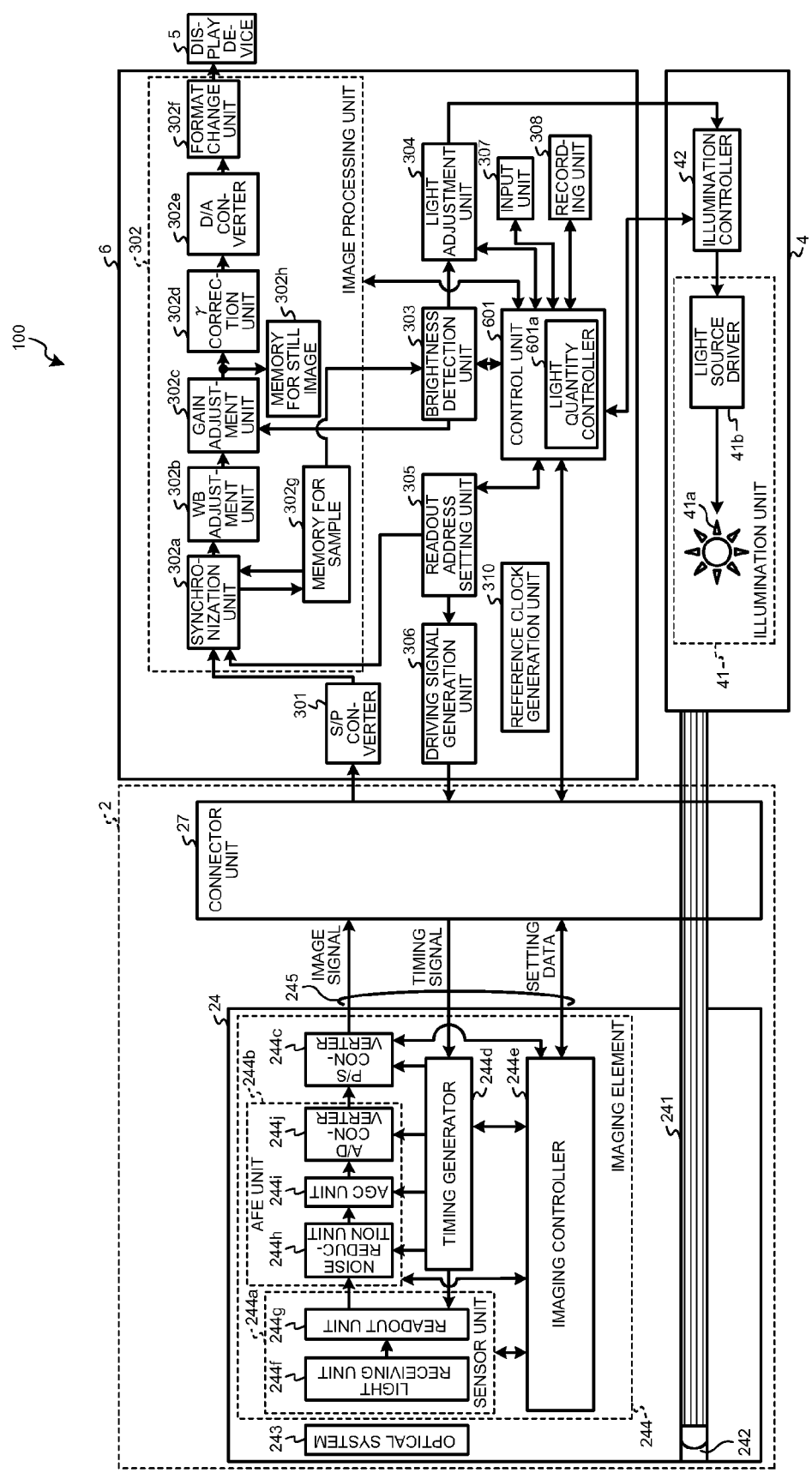
FIG. 9 is a block diagram illustrating a function structure of a main part of an endoscope system according to a second embodiment of the present invention.

FIG. 9 is a block diagram illustrating a function structure of a main part of the endoscope system according to the second embodiment. An endoscope system 100 illustrated in FIG. 9 includes the endoscope 2, the light source device 4, the display device 5, and a processing device 6.

The processing device 6 includes the S/P converter 301, the image processing unit 302, the brightness detection unit 303, the light adjustment unit 304, the readout address setting unit 305, the driving signal generation unit 306, the input unit 307, the recording unit 308, the reference clock generation unit 310, and a control unit 601.

The control unit 601 is composed of a CPU or the like, and controls the driving of the components including the imaging element 244 and the light source device 4 and controls the input/output of the information relative to the components. The control unit 601 transmits the setting data for the image-capture control to the imaging controller 244e via a specified signal line included in the set of cables 245. The control unit 601 outputs a synchronization signal including the exposure timing and the readout timing of each line of the imaging element 244 to the light source device 4. The control unit 601 has a light quantity controller 601a.

The light quantity controller 601a controls the light quantity of the illumination light emitted from the illumination unit 41 of the light source device 4. Specifically, the light quantity controller 601a calculates the light quantity of the illumination light emitted from the illumination unit 41, on the basis of the signal related to the brightness level input from the brightness detection unit 303, and then outputs a light quantity signal representing the calculated light quantity to the illumination controller 42.

Reference will be made to the relation between the illumination light emitted from the light source device 4 and the exposure period and the readout period of the imaging element 244 during the image-capture time of the endoscope system 100 having the above structure.

Figure 10:
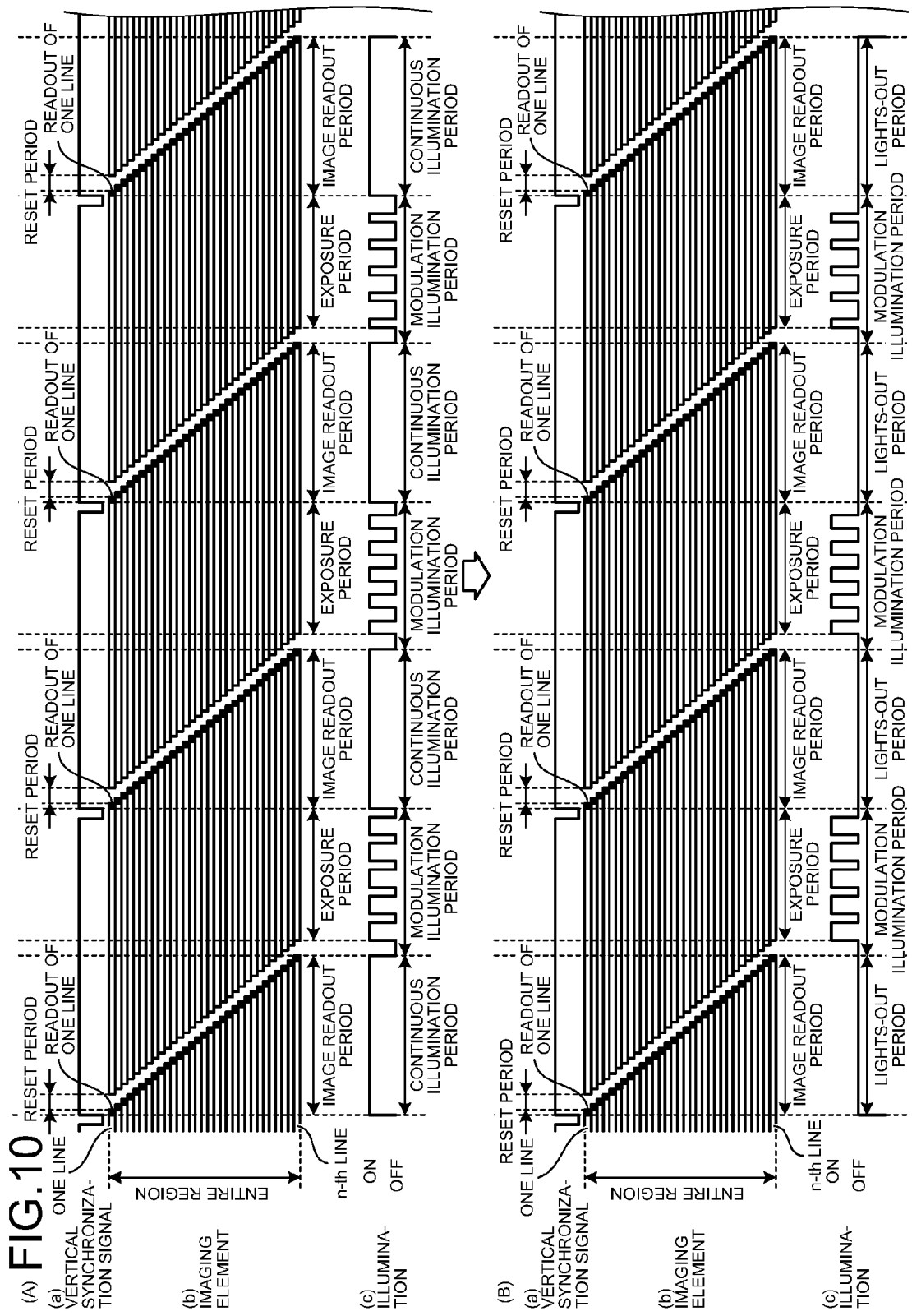
FIG. 10 is a diagram representing the relation between the illumination light emitted from the light source device with the illuminance of the light changing from high illuminance to low illuminance, and the exposure period and the readout period of the imaging element during the image-capture time of the endoscope system according to the second embodiment of the present invention.

FIG. 10 is a diagram illustrating the relation between the illumination light emitted from the light source device 4 with the illuminance varying from high illuminance to low illuminance, and the exposure period and the readout period of the imaging element 244 during the image-capture time of the endoscope system 100. In FIG. 10, (a) represents a vertical synchronization signal, (b) represents the exposure period and the readout timing of each line of the imaging element 244, and (c) represents the illumination period of the illumination light emitted from the light source device 4.

As illustrated in FIG. 10, in the case of capturing an image for one frame period, the imaging element 244 sequentially reads out the accumulated charges for every horizontal line. Therefore, as illustrated in FIG. 10(A), when the light source device 4 emits the illumination light at the high illuminance, the illumination controller 42 causes the illumination unit 41 to continuously emit the illumination light so that the intensity of the illumination light emitted from the illumination unit 41 is kept constant in the entire readout period where the readout unit 244g reads out the horizontal lines of the light receiving unit 244f in one frame period.

On the other hand, when the light source device 4 emits the illumination light at the high illuminance, the illumination controller 42 performs the PWM control on the illumination unit 41 so that the illumination unit 41 emits the illumination light while the light receiving unit 244f is in the entire line simultaneous exposure period in one frame period as illustrated in FIG. 10(A).

When the light source device 4 emits the illumination light at the low illuminance, the illumination controller 42 causes the illumination unit 41 to stop the illumination light so that the light is turned off in the entire readout period where the readout unit 244g reads out the horizontal lines of the light receiving unit 244f in one frame period as illustrated in FIG. 10(B).

On the other hand, when light source device 4 emits the illumination light at the low illuminance, the illumination controller 42 performs the PWM control on the illumination unit 41 so that the illumination unit 41 emits the illumination light in the entire simultaneous exposure period where the light receiving unit 244f is exposed to light in one frame period as illustrated in FIG. 10(B).

Here, reference will be made to a method in which the illumination controller 42 switches the illuminance of the illumination light of the light source device 4 from the high illuminance to the low illuminance on the basis of the light quantity signal related to the light quantity input from the light quantity controller 601a.

Figure 11:
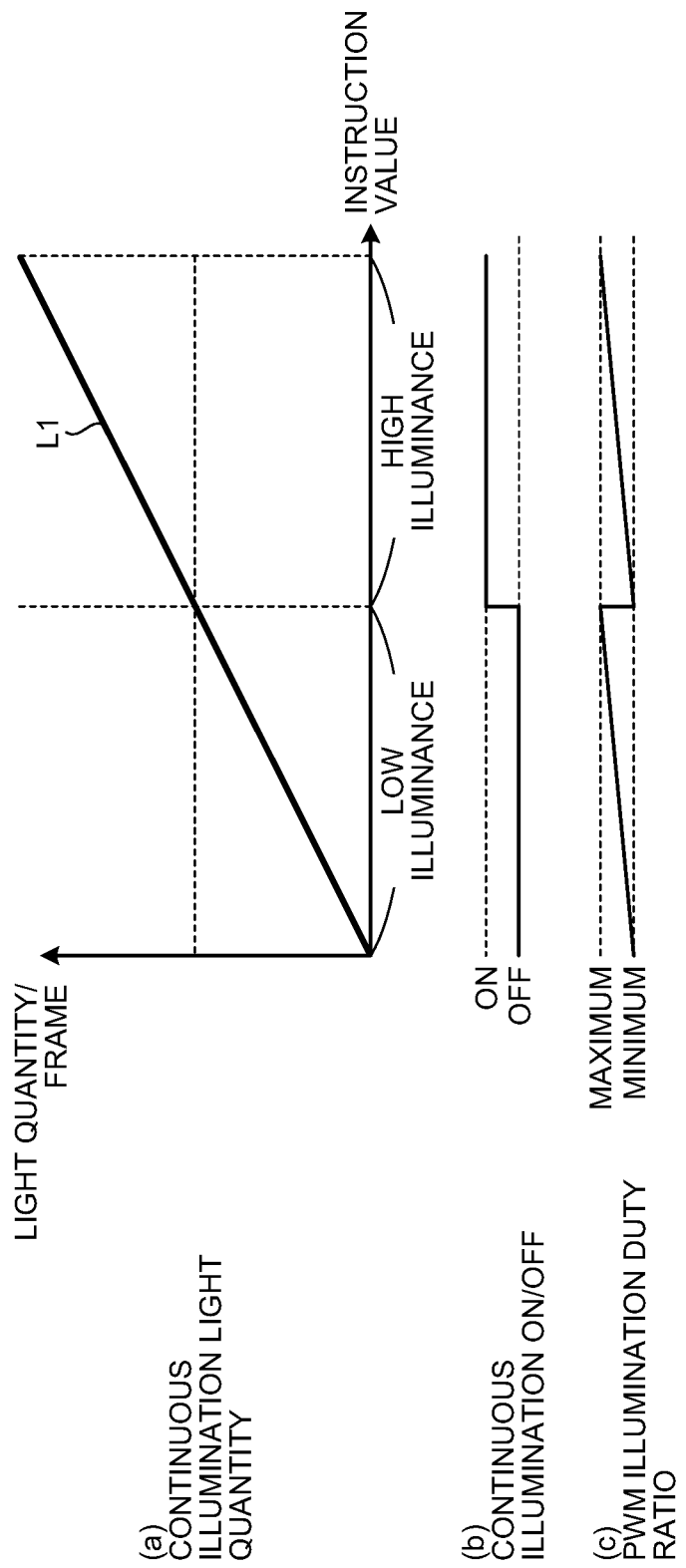
FIG. 11 is a diagram for describing how to change the illuminance of the illumination light emitted from the light source device from high illuminance to low illuminance by the illumination controller on the basis of a light quantity signal input from a light quantity controller in the endoscope system according to the second embodiment of the present invention.

FIG. 11 is a diagram for describing a method of switching the illuminance of the illumination light of the light source device 4 from the high illuminance to the low illuminance by the illumination controller 42 on the basis of the light quantity signal related to the light quantity input from the light quantity controller 601a. In FIG. 11, a vertical axis of (a) represents the light quantity per frame while a horizontal axis thereof represents the instruction value of the light quantity of the illumination light per unit time, which is input from the light quantity controller 601a. In FIG. 11, (b) represents the on state or the off state of the continuous illumination light emitted from the illumination unit 41. In FIG. 11, (c) represents the duty ratio of the illumination unit 41 controlled by the illumination controller 42 in the PWM control. Moreover, a line L1 represents the relation between the light quantity per frame and the instruction value corresponding to the light quantity signal input from the light quantity controller 601a.

When the intensity of the illumination light emitted from the illumination unit 41 is switched from the high illuminance to the low illuminance (FIG. 10(A)→FIG. 10(B)), the illumination controller 42 changes the intensity of the illumination light emitted from the illumination unit 41 so that the light quantity of the continuous illumination at the high illuminance and the maximum light quantity by the PWM control at the low illuminance (when the duty ratio is the maximum) are made approximately equal to each other as illustrated in FIG. 11. Specifically, in the case where the illumination unit 41 emits the illumination light at the high illuminance, the illumination controller 42 changes the illuminance of the illumination light emitted from the illumination unit 41 to the high illuminance by controlling the light quantity of the illumination light emitted from the illumination unit 41 so that the duty ratio of the light quantity of the light emitted from the illumination unit 41 is gradually decreased by the PWM control for every frame period of the imaging element 244 and when the duty ratio becomes the minimum (for example, zero), the light quantity of the continuous illumination at the high illuminance and the maximum light quantity by the PWM control at the low illuminance become approximately equal to each other. In this case, the maximum light quantity of the illumination light by the PWM control is set by the maximum duty ratio or the pulse width. The illumination controller 42 stops the illumination light from the illumination unit 41 to turn off the light in the entire readout period where the readout unit 244g reads out the horizontal lines of the light receiving unit 244f in one frame period.

According to the second embodiment of the present invention described above, the illumination controller 42 can control the intensity of the illumination light of the illumination unit 41 by the PWM control in the period where the readout unit 244g does not read out the light receiving unit 244f. As a result, the exposure unevenness of the image can be prevented.

Moreover, according to the second embodiment, when the illuminance of the illumination light emitted from the illumination unit 41 is switched from the high illuminance to the low illuminance, the illumination controller 42 changes the intensity of the illumination light emitted from the illumination unit 41 by controlling the light quantity of the light emitted from the illumination unit 41 for every frame period so that the light quantity of the continuous illumination at the high illuminance becomes approximately equal to the maximum light quantity by the PWM control at the low illuminance. As a result, even when the illumination light emitted from the illumination unit 41 is switched from the high illuminance to the low illuminance, the intensity of the illumination light can be changed smoothly and continuously.

Third Embodiment

Next, a third embodiment of the present invention is described. In an endoscope system according to the third embodiment, the light source device emits the illumination light in a field sequential method. Thus, the endoscope system according to the third embodiment is described first, and then the illumination period and the illumination method for the light source device are described. The same reference numerals are used to refer to the same parts as those of the first embodiment.

Figure 12:
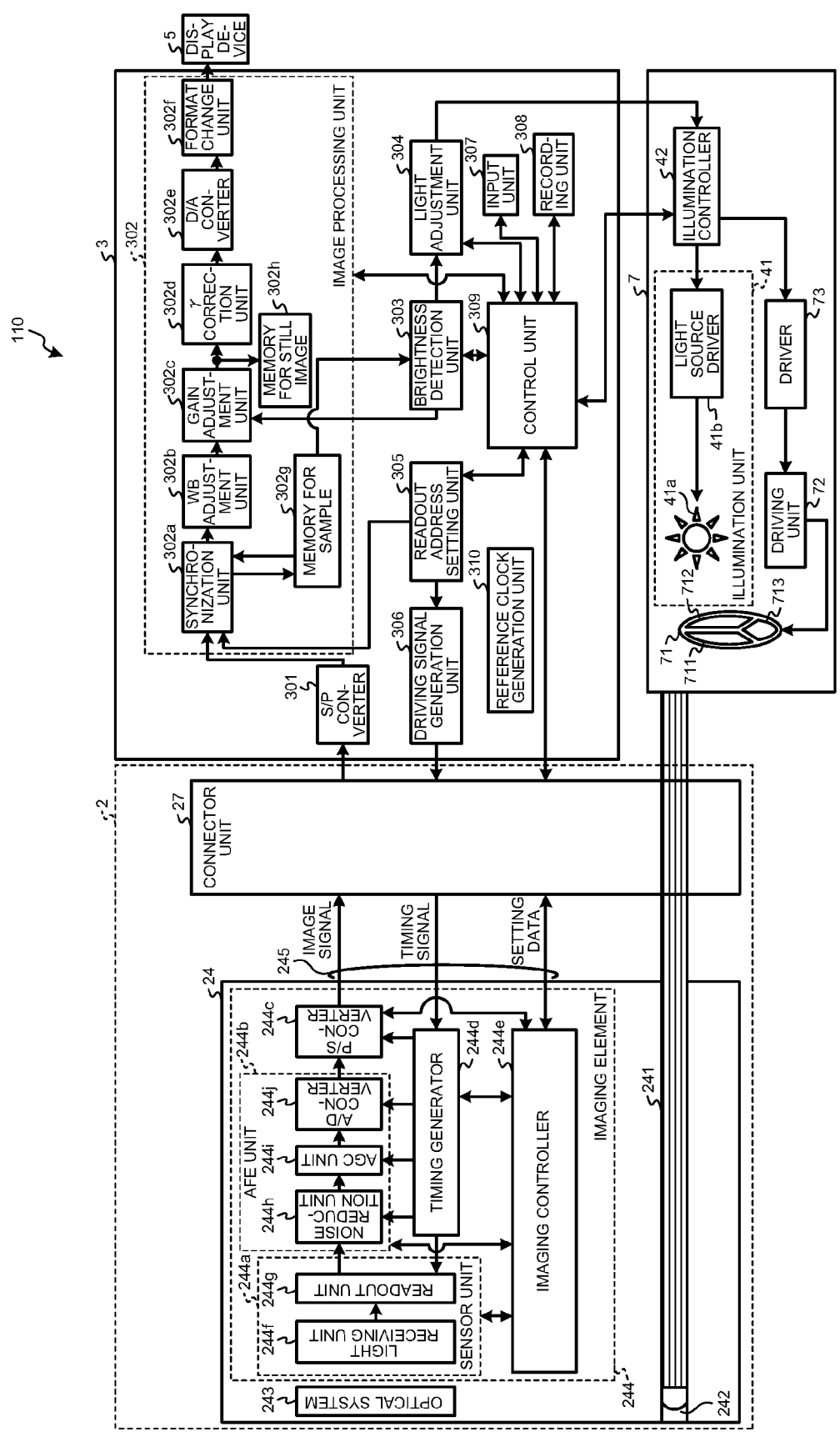
FIG. 12 is a block diagram illustrating a function structure of a main part of an endoscope system according to a third embodiment of the present invention.

FIG. 12 is a block diagram illustrating a function structure of a main part of the endoscope system according to the third embodiment. An endoscope system 110 illustrated in FIG. 12 includes the endoscope 2, the processing device 3, the display device 5, and a light source device 7.

The light source device 7 includes the illumination unit 41, a rotation filter 71, a driving unit 72, a driver 73, and an illumination controller 74.

The illumination unit 41 emits white light toward the rotation filter 71 under the control of the illumination controller 74. The white light emitted from the illumination unit 41 is delivered from an end of the end portion 24 toward a subject via the rotation filter 71, a focusing lens (not shown), and the light guide 241.

The rotation filter 71 is disposed on an optical path of the white light emitted from the illumination unit 41, and rotates to transmit only light with a specified wavelength band out of the white light emitted from the illumination unit 41. Specifically, the rotation filter 71 has a red filter 711, a green filter 712, and a blue filter 713 that transmits light having red (R), green (G), and blue (B) wavelength bands, respectively. The rotation filter 71 rotates to sequentially transmit light having red, green, and blue wavelength bands (for example, red: 600 nm to 700 nm, green: 500 nm to 600 nm, blue: 400 nm to 500 nm). Thus, out of the white light emitted from the illumination unit 41, any of the narrow-banded red light, green light, and blue light can be delivered sequentially to the endoscope 2.

The driving unit 72 is composed of a stepping motor or a DC motor, for example, and rotates the rotation filter 71. The driver 73 supplies specified current to the driving unit 72 under the control of the illumination controller 74.

The illumination controller 74 keeps the intensity of the illumination light emitted from the illumination unit 41 constant in at least a part of the readout period where the readout unit 244g reads out the horizontal lines of the light receiving unit 244f in one frame period while the illumination controller 74 variably controls the intensity of the illumination light emitted from the illumination unit 41 outside the readout period.

Reference will be made to the relation between the illumination light emitted from the light source device 7 and the exposure or readout timing of the imaging element 244 during the image-capture time of the endoscope system 110 with the above structure.

Figure 13:
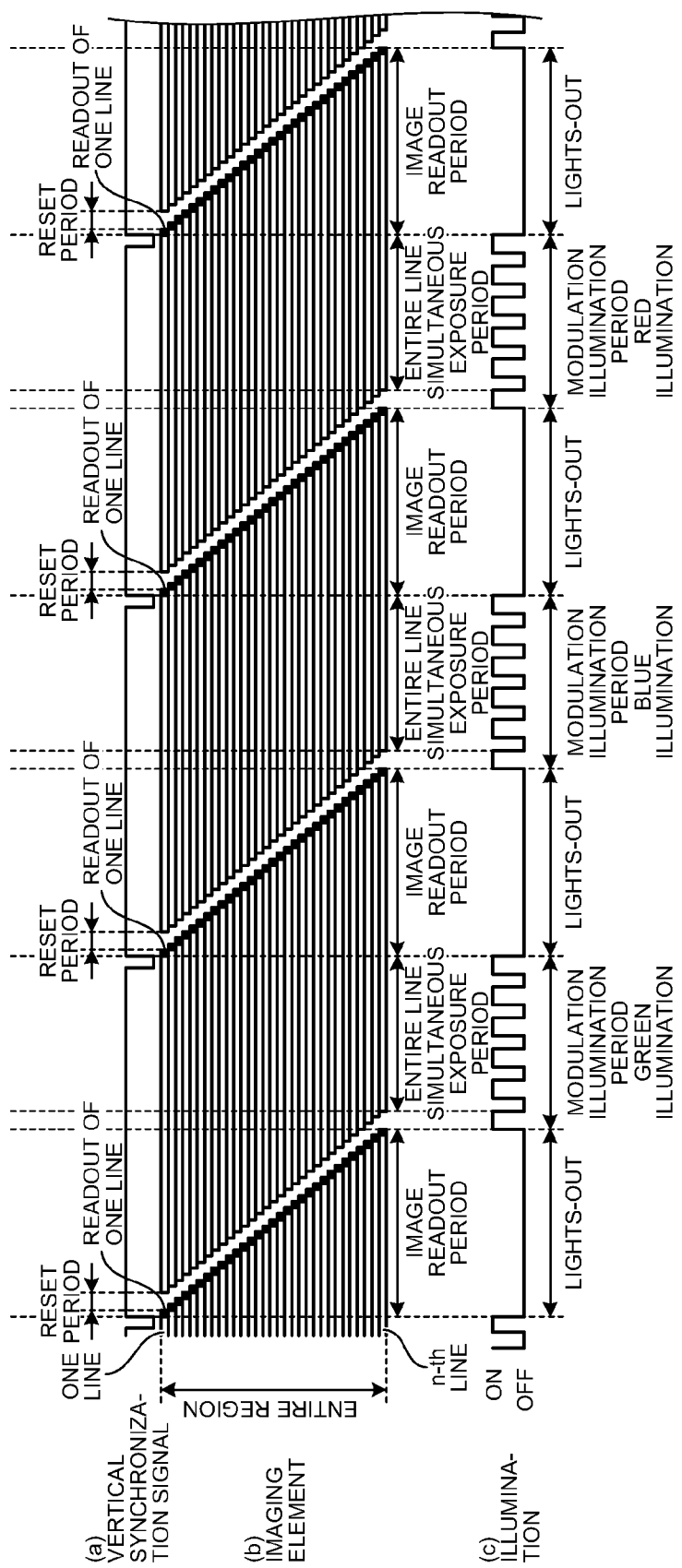
FIG. 13 is a diagram representing the relation between the illumination light emitted from the light source device and the exposure period and the readout period of the imaging element during the image-capture time of the endoscope system according to the third embodiment of the present invention.

FIG. 13 is a diagram illustrating the relation between the illumination light emitted from the light source device 7 and the exposure period and the readout period of the imaging element 244 during the image-capture time of the endoscope system 1. In FIG. 13, (a) represents a vertical synchronization signal, (b) represents the exposure period and the readout timing of each line of the imaging element 244, and (c) represents the illumination period and the wavelength band of the illumination light emitted from the light source device 7.

As illustrated in FIG. 13, in the case of continuously capturing images in plural frame periods, the imaging element 244 sequentially reads out the accumulated charges for every horizontal line. Moreover, the illumination controller 74 changes the band of the illumination light by rotating the rotation filter 71 for each frame (green→blue→red). Therefore, as illustrated in FIG. 13, the illumination controller 74 stops the illumination light emitted from the illumination unit 41 to turn off the light in the entire readout period where the readout unit 244g reads out the horizontal lines of the light receiving unit 244f in one frame period.

On the other hand, the illumination controller 74 causes the illumination unit 41 to emit the illumination light by performing the PWM control on the illumination unit 41 in the entire line simultaneous exposure period other than the readout period where the readout unit 244g reads out the horizontal lines of the light receiving unit 244f in one frame period as illustrated in FIG. 13.

According to the third embodiment of the present invention described above, even in the case of the field sequential illumination using the plural wavelength bands, the occurrence of color mixture between the frames can be prevented certainly and the exposure unevenness of the image can be prevented.

The third embodiment is also applicable when the light emitted from the light source device 7 is the NBI (Narrow Band Imaging) illumination light having a different wavelength band from the white light and having two kinds of bands of green and blue light that has been narrow-banded by a narrow bandpass filter.

Fourth Embodiment

A fourth embodiment of the present invention is described next. An endoscope system according to the fourth embodiment of the present invention is different from that of the second embodiment in the illumination method for the light source device. Thus, here, the endoscope system according to the fourth embodiment is described first and then, the illumination method during the image-capture time of the endoscope system is described. The same reference numerals are used to refer to the same parts as those of the first embodiment.

Figure 14:
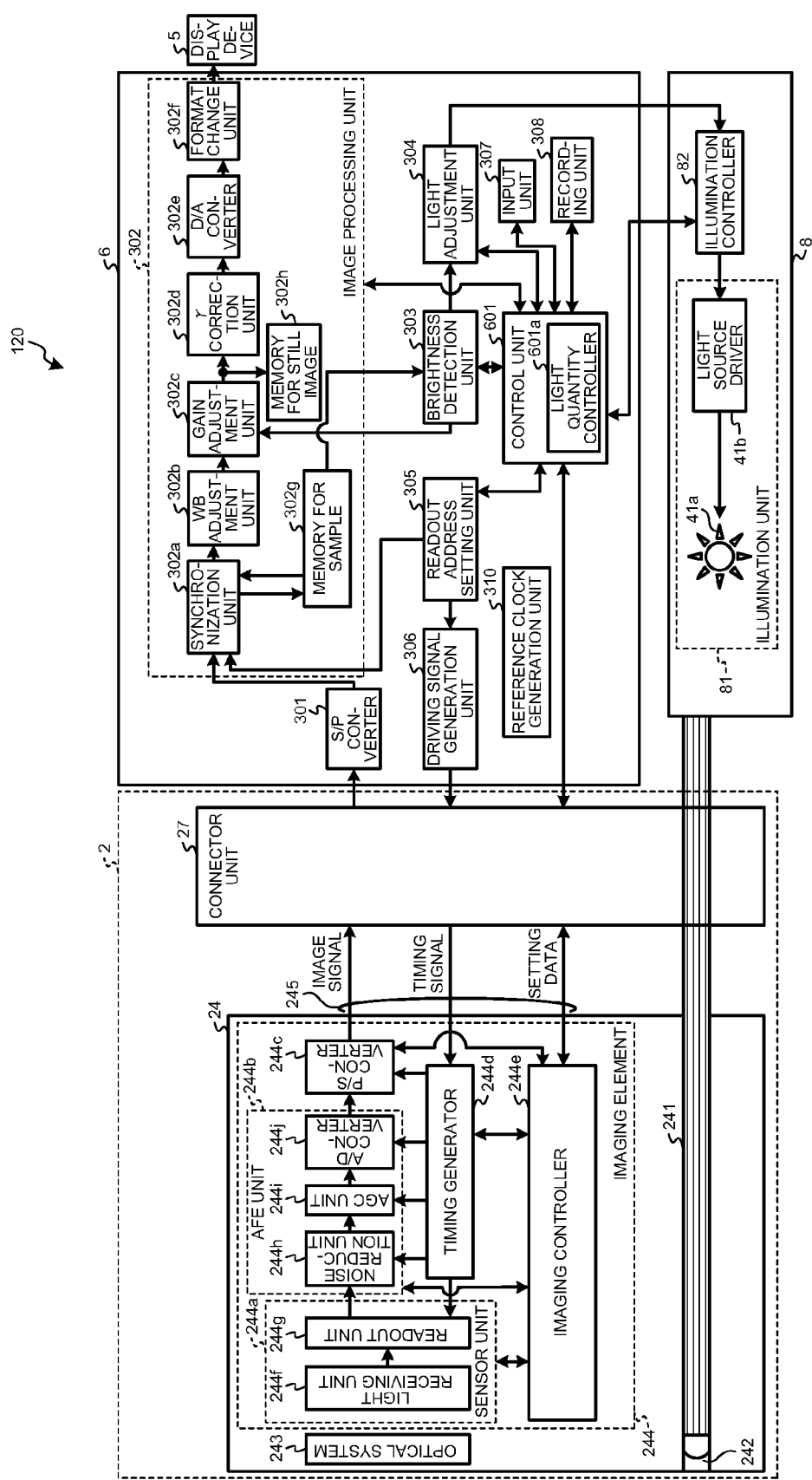
FIG. 14 is a block diagram illustrating a function structure of a main part of an endoscope system according to a fourth embodiment of the present invention.

FIG. 14 is a block diagram illustrating the function structure of a main part of the endoscope system according to the fourth embodiment. An endoscope system 120 illustrated in FIG. 14 includes the endoscope 2, the display device 5, the processing device 6, and a light source device 8. The light source device 8 includes an illumination unit 81 and an illumination controller 82.

The illumination unit 81 emits the illumination light that illuminates the subject. The illumination unit 81 can perform a constant-intensity illumination mode and a variable illumination mode. In the constant-intensity illumination mode, the intensity of the illumination light is maintained in the readout period and outside the readout period within one frame or one field period of the imaging element 244. In the variable illumination mode, the illumination time and the intensity of the illumination light can be changed outside the readout period within one frame or one field period of the imaging element 244. The illumination unit 81 includes a light source 41a and a light source driver 41b. Specifically, in the constant-intensity illumination mode, the illumination unit 81 emits the illumination light while the intensity of the light emitted from the light source 41a is kept constant by keeping the level of the current supplied by the light source driver 41b to be constant in the readout period where the readout unit 244g of the imaging element 244 reads out the horizontal lines of the light receiving unit 244f and outside the readout period. On the other hand, in the variable illumination mode, the illumination unit 81 emits the illumination light while the illumination time and the intensity of the illumination light emitted from the illumination unit 41 are changed by performing the PWM control on the light source driver 41b outside the period where the readout unit 244g of the imaging element 244 reads out the horizontal lines of the light receiving unit 244f.

The illumination controller 82 causes the illumination unit 81 to execute the constant-intensity illumination mode and the variable illumination mode on the basis of the light quantity controlled by the light quantity controller 601a; when the mode of the illumination unit 81 is changed from the constant-intensity illumination mode to the variable illumination mode, the intensity and the time of the illumination light of the illumination unit 81 in the variable illumination mode are set so that the light quantity of the illumination light emitted from the illumination unit 81 in one frame or in one field period of the imaging element 244 becomes the same. Specifically, the illumination controller 82 controls to keep the intensity of the illumination light emitted from the illumination unit 81 constant by controlling to keep the level of the current supplied to the light source 41a by the light source driver 41b constant in and outside the period where the readout unit 244g of the imaging element 244 reads out the horizontal lines of the light receiving unit 244f. On the other hand, the illumination controller 82 performs the PWM control on the illumination time and the intensity of the illumination light emitted from the illumination unit 41 outside the period where the readout unit 244g of the imaging element 244 reads out the horizontal lines of the light receiving unit 244f. For preventing the color temperature from largely changing due to the current control, the table of the value of current to be supplied relative to the light quantity is recorded in a recording unit, which is not shown, of the illumination controller 82.

Reference will be made to the relation between the illumination light emitted from the light source device 8 and the exposure or readout timing of the imaging element 244 during the image-capture time of the endoscope system 120 having the above structure.

Figure 15:
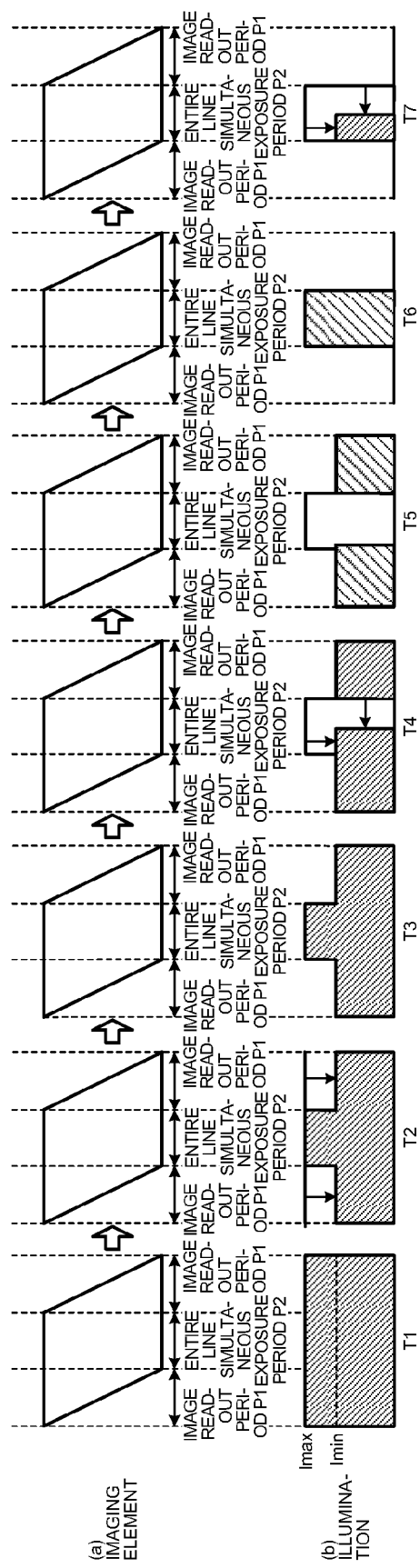
FIG. 15 is a diagram representing the relation between the illumination light emitted from the light source device and the exposure period and the readout period of the imaging element during the image-capture time of the endoscope system according to the fourth embodiment of the present invention.

FIG. 15 is a diagram illustrating the relation between the illumination light emitted from the light source device 8 and the exposure period and the readout period of the imaging element 244 during the image-capture time of the endoscope system 120. In FIG. 15, (a) schematically illustrates the timing of the exposure period of each line of the imaging element 244. In FIG. 15, (b) illustrates the illumination period of the illumination light emitted from the light source device 4. Reference will be made below to the case where all the lines including a dummy line of an optical black region or an invalid region of the imaging element 244 are sequentially read out from the top to the bottom in a progressive manner. Moreover, reference will be made below to the case in which the light quantity of the illumination light is gradually decreased.

As illustrated in FIG. 15, the illumination controller 82 causes the light source 41a to continuously illuminate (CW lighting) (period T1 in FIG. 15) in a image readout period P1 and an entire line simultaneous exposure period P2 by controlling the drive of the light source driver 41b to supply current while the level of the current supplied from the light source driver 41b to the light source 41a is set to the maximum (maximum current $I_{max}$).

Subsequently, on the basis of the light quantity of the instruction signal input from the light quantity controller 601a, the illumination controller 82 controls to reduce the light quantity of the illumination light emitted from the illumination unit 41 in the image readout period P1 of the imaging element 244 (period T2 in FIG. 15). Specifically, on the basis of the light quantity of the instruction signal input from the light quantity controller 601a, the illumination controller 82 supplies the current from the maximum level to the minimum level (minimum current $I_{min}$) by gradually decreasing the current level of the current supplied by the light source driver 41b to the light source 41a in the image readout period P1 of the imaging element 244, and thus controls the drive of the illumination unit 81 separately in the entire line simultaneous exposure period P2 and the image readout period P1 (FIG. 15 (period T2)→FIG. 15 (period T3)). Here, the minimum current ($I_{min}$) refers to the minimum current value that can be provided by the light source driver 41b or the minimum current value at which the lighting of the light source 41a is assured. On this occasion, for preventing the current level from differing in the entire line simultaneous exposure period P2 and in the image readout period P1 to vary the color temperature, the correction is conducted with reference to the current value table stored in the recording unit, which is not shown, in the illumination controller 82.

After that, the illumination controller 82 decreases the light quantity of the illumination light emitted from the illumination unit 81 in the entire line simultaneous exposure period P2 by the current light adjustment and the PWM light adjustment in the entire line simultaneous exposure period P2 of the imaging element 244 (FIG. 15 (period T3)→FIG. 15 (period T4)). Specifically, in the entire line simultaneous exposure period P2 of the imaging element 244, the illumination controller 82 supplies current while setting the level of the current supplied to the light source 41a by the light source driver 41b from the maximum level to the minimum level. Moreover, in the entire line simultaneous exposure period P2 of the imaging element 244, the illumination controller 82 conducts the PWM control on the illumination unit 81 and reduces the pulse width of the illumination light emitted from the illumination unit 81, whereby the illumination time of the entire line simultaneous exposure period P2 is reduced gradually.

Subsequently, in the image readout period P1 and the entire line simultaneous exposure period P2 of the imaging element 244, the illumination controller 82 further decreases the light quantity of the illumination light emitted from the illumination unit 81 in the entire line simultaneous exposure period P2 and the image readout period P1 by the PWM light adjustment (FIG. 15 (period T4)→FIG. 15 (period T5)). Specifically, in the entire line simultaneous exposure period P2 and the image readout period P1 of the imaging element 244, the illumination controller 82 conducts the PWM control on the illumination unit 81 and decreases the light quantity of the illumination light emitted from the illumination unit 81 in entire line simultaneous exposure period P2 and the image readout period P1.

After that, the illumination controller 82 causes the illumination unit 81 to stop the light by the current light adjustment and the PWM light adjustment in the image readout period P1, and sets the level of the current supplied to the light source 41a by the light source driver 41b in the entire line simultaneous exposure period P2 to the maximum level and moreover performs the PWM control on the illumination unit 81 to maximize the pulse width of the illumination light emitted from the illumination unit 81; thus, the mode is switched from the constant-intensity illumination mode to the variable illumination mode (FIG. 15 (period T5)→FIG. 15 (period T6)). In this case, the illumination controller 82 changes the mode by setting the intensity and the time of the illumination light by the illumination unit 81 so that the light quantity ($I_{min} \times P1$) in the image readout period P1 and the light quantity ($I_{max} \times P2$) in the entire line simultaneous exposure period P2 become equal to each other ($I_{min} \times P1 = I_{max} \times P2$). This can continuously change the light quantity curve of the illumination light emitted from the illumination unit 81.

Next, in the entire line simultaneous exposure period P2 of the imaging element 244, the illumination controller 82 decreases the light quantity of the illumination light emitted from the illumination unit 81 in the entire line simultaneous exposure period P2 by the current light adjustment of the illumination unit 81 (FIG. 15 (period T6)→FIG. 15 (period T7)).

According to the fourth embodiment of the present invention described above, when the mode of the illumination unit 81 is switched from the constant-intensity illumination mode to the variable illumination mode, the intensity and the time of the illumination light in the variable illumination mode are set so that the light quantity of the illumination light emitted from the illumination unit 81 is the same in one frame period. This can continuously change the light quantity curve of the illumination light emitted from the illumination unit 81. As a result, the bright and dark stripes in one screen can be prevented and the light adjustment function that can narrow sufficient light quantity can be achieved.

In the fourth embodiment of the present invention, the present invention is applicable to any imaging element that satisfies the condition where the light quantity ($I_{max} \times P2$) in the entire line simultaneous exposure period P2 is equal to or more than the light quantity ($I_{min} \times P1$) in the image readout period P1 ($I_{max} \times P2 \geq I_{min} \times P1$). In this case, the light quantity ($I_{P1}$ (current in the image readout period P1)×P1) in the image readout period P1 may be the same as the light quantity ($I_{P2}$ (current in the entire line simultaneous exposure period P2)× P2) in the entire line simultaneous exposure period P2($I_{P1} \times P1 = I_{P2} \times P2$).

Fifth Embodiment

A fifth embodiment of the present invention is described. The fifth embodiment is different from the fourth embodiment in the illumination method for the light source device. Therefore, reference will be made below to the illumination method for the light source device in an endoscope system according to the fifth embodiment. The same reference numerals are used to refer to the same parts as those of the fourth embodiment.

Figure 16:
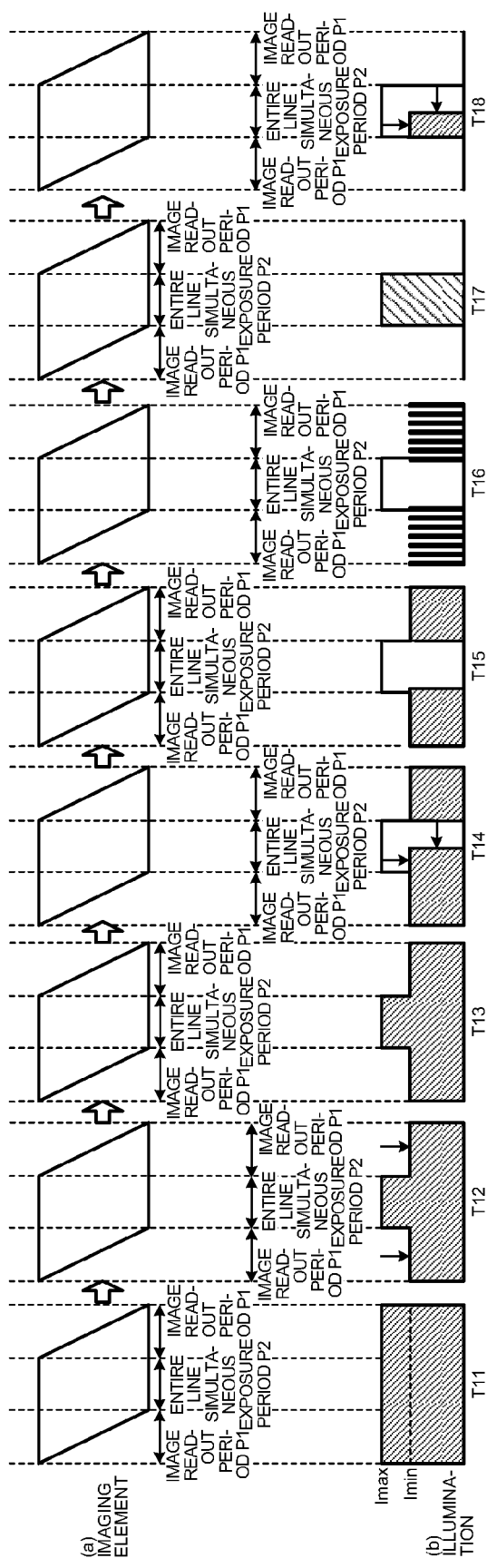
FIG. 16 is a diagram representing the relation between the illumination light emitted from the light source device and the exposure period and the readout period of the imaging element during the image-capture time of the endoscope system according to a fifth embodiment of the present invention.

FIG. 16 is a diagram illustrating the relation between the illumination light emitted from the light source device 8 and the exposure period and the readout period of the imaging element 244 during the image-capture time of the endoscope system 120 according to the fifth embodiment. In FIG. 16, (a) schematically illustrates the timing of the exposure period of each line of the imaging element 244. In FIG. 16, (b) illustrates the illumination period of the illumination light emitted from the light source device 8. Reference will be made below to the case where all the lines including a dummy line of an optical black region or an invalid region of the imaging element 244 are sequentially read out from the top to the bottom in a progressive manner. Moreover, reference will be made below to the case in which the light quantity of the illumination light is gradually decreased.

The periods T11 to T15 in FIG. 16 correspond to the periods T1 to T5 in FIG. 15, respectively.

Subsequently, the illumination controller 82 switches the mode from the constant-intensity illumination mode to the line unit illumination mode where the illumination time of the illumination light emitted from the illumination unit 81 is kept constant for every horizontal line of the imaging element 244 by conducting the PWM control on the illumination unit 81 on the basis of the light quantity of the instruction signal input from the light quantity controller 601a (FIG. 16 (period T15)→FIG. 16 (period T16)).

Figure 17:
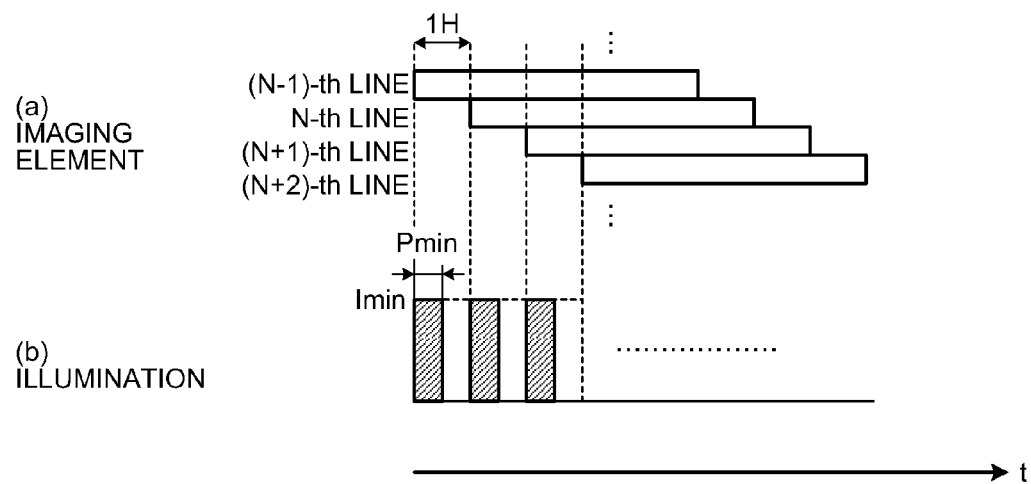
FIG. 17 is a magnified diagram schematically representing the relation between the illumination light emitted from the illumination unit and each horizontal line of the imaging element in some line periods in the period T16 of FIG. 16.

FIG. 17 is a magnified diagram schematically illustrating the relation between the illumination light emitted from the illumination unit 81 and each horizontal line of the imaging element 244 in the image readout period in the period T16 of FIG. 16.

As illustrated in FIG. 17, the illumination controller 82 conducts the PWM control on the illumination unit 81 so that the illumination unit 81 emits the illumination light in synchronization with the timing at which the readout unit 244g reads out each horizontal line of the light receiving unit 244f. Specifically, by gradually narrowing down the pulse width until the minimum pulse width $P_{min}$ that can be provided by the light source driver 41b, the illumination controller 82 causes the illumination unit 81 to emit the illumination light with the PWM light adjustment in synchronization with the timing at which the readout unit 244g reads out each horizontal line (for example, (N−1)-th line (N is a natural number)) of the light receiving unit 244f.

After that, the illumination controller 82 causes the illumination unit 81 to stop the light emission in the image readout period P1; in the entire line simultaneous exposure period P2, the illumination controller 82 maximizes the level ($I_{max}$) of the current supplied to the light source 41a by the light source driver 41b and maximizes the pulse width ($PWM_{max}$) of the light emitted from the illumination unit 81 by conducting the PWM control on the illumination unit 81, so that the mode of the illumination unit 81 is switched from the line unit illumination mode to the variable illumination mode (FIG. 16 (period T16)→FIG. 16 (period T17)). In this case, the illumination controller 82 switches the mode by setting the intensity and the time of the illumination light from the illumination unit 81 so that the light quantity in the image readout period P1 ($I_{min} \times P1 \times P_{min}/1H$) and the light quantity in the entire line simultaneous exposure period P2 ($I_{max} \times P2$) become the same ($I_{max} \times P2 = I_{min} \times P1 \times P_{min}/1H$). This can continuously change the light quantity curve of the illumination light emitted from the illumination unit 81.

Subsequently, the periods T17 and T18 correspond to the periods T6 and T7 in FIG. 15, respectively.

According to the sixth embodiment of the present invention described above, the illumination controller 82 switches the mode by setting the intensity and the time of the illumination light from the illumination unit 81 so that the light quantity in the image readout period P1 and the light quantity in the entire line simultaneous exposure period P2 become the same ($I_{min} \times P2 = I_{min} \times P1 \times P_{min}/1H$). This can continuously change the light quantity curve of the illumination light emitted from the illumination unit 81. As a result, the bright and dark stripes in one screen can be prevented and the light adjustment function that can narrow sufficient light quantity can be achieved.

Moreover, according to the sixth embodiment of the present invention, even the imaging element 244 with a short entire line simultaneous exposure period P2 can adjust the light while maintaining the continuous light quantity curve.

In the sixth embodiment of the present invention, the present invention can be applied as long as the imaging element satisfies the condition that the light quantity ($I_{max} \times P2$) in the entire line simultaneous exposure period P2 is more than or equal to the light quantity ($I_{min} \times P1$) in the image readout period P1, which is ($I_{min} \times P1 \times P_{min}/1H$). In this case, the light quantity ($I_{P1} \times P1$) in the image readout period P1 may be the same as the light quantity ($I_{P2} \times P2 \times C$ (pulse width of LED in 1H)/1H) in the entire line simultaneous exposure period P2 ($I_{P1} \times P1 = I_{P2} \times P2 \times C/1H$).

Other Embodiments

The present invention is also applicable to the case in which the readout unit reads out from the light receiving unit in an interlacing manner. In this case, the aforementioned one frame period may be replaced with one field period.

In the present invention, the processing device and the light source device may be integrated.

In the present invention, an LED as the illumination unit may be provided at the end portion, and the imaging controller may conduct the PWM control on this LED.

In the present invention, the control unit may conduct the PWM control on the illumination unit on the basis of the light adjustment signal and the exposure or readout timing of the imaging element.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging system comprising:
    an illumination unit configured to emit illumination light for illuminating a subject;
    a light receiving unit in which pixels are arranged two-dimensionally, each pixel being configured to receive light and generate an electric signal by performing photoelectric conversion of the light;
    a readout unit configured to sequentially read out the electric signal from the light receiving unit for every horizontal line;
    an illumination controller configured to keep intensity of the illumination light emitted from the illumination unit constant in at least a part of a readout period where the readout unit reads out the horizontal line of the light receiving unit in one frame or one field period, and configured to variably control an illumination time of the illumination light emitted from the illumination unit, outside the readout period;
    an image processing unit configured to perform a specified image process on the electric signal read out by the readout unit and generate an image of the subject; and
    a brightness detection unit configured to detect brightness of the subject included in the image generated by the image processing unit,
    wherein
        the readout period is a period where the readout unit reads out the horizontal line of the light receiving unit as a target of the image processing unit, and
        the illumination controller is configured to variably control the intensity and timing of the illumination light based on the brightness of the subject detected by the brightness detection unit.

2. The imaging system according to claim 1, further comprising a light quantity controller configured to control light quantity of the illumination light emitted from the illumination unit in one frame or one field period,
    wherein
        the illumination controller is configured to perform continuous illumination in which the intensity of the illumination light is kept constant in the readout period in the one frame or one field period, and is configured to perform modulation illumination in which the illumination time of the illumination is modulated outside the readout period in the one frame or one field period, and
        in the case where the light quantity is decreased in the one frame or one field period based on the light quantity by the light quantity controller, the intensity of the continuous illumination and the illumination time of the modulation illumination are set in such a way that the light quantity in the one frame or one field period is the same when the illumination unit performs the modulation illumination to minimize the illumination time of the illumination light outside the readout period.

3. The imaging system according to claim 2, further comprising a light quantity controller configured to control the light quantity of the illumination light emitted from the illumination unit in one frame or one field period, wherein the illumination controller is configured to perform a constant-intensity illumination mode in which the intensity of the illumination light is kept constant in and outside the readout period in the one frame or one field period, and is configured to perform a variable illumination mode in which the intensity of the illumination light emitted from the illumination unit is kept constant in at least a part of the readout period and the illumination time of the illumination light emitted from the illumination unit is variably controlled outside the readout period, and when switching from the constant-intensity illumination mode to the variable illumination mode based on the light quantity controlled by the light quantity controller, the intensity and the illumination time of the illumination light in the variable illumination mode are set in such a way that the light quantity is the same in the one frame or one field period.

4. The imaging system according to claim 3, wherein the illumination controller is configured to further perform a line unit illumination mode in which the illumination time of the illumination light is kept constant for every horizontal line in the readout period in the one frame or one field period, and when switching among the constant-intensity illumination mode, the variable illumination mode, and the line unit illumination mode based on the light quantity controlled by the light quantity controller, the light quantity is the same in the one frame or one field period.

5. The imaging system according to claim 1, further comprising a synchronization signal generation unit configured to output a synchronization signal including readout timing of the electric signal by the readout unit, to the illumination controller.

6. The imaging system according to claim 1, wherein the illumination unit is a solid light source.

7. The imaging system according to claim 6, wherein the illumination controller is configured to perform PWM control on the solid light source to variably control the intensity and timing of the illumination light.

* * * * *